US012667471B2

(12) United States Patent
Herr et al.

(10) Patent No.: US 12,667,471 B2
(45) Date of Patent: Jun. 30, 2026

(54) MECHANONEURAL INTERFACES FOR PROSTHETIC CONTROL

(71) Applicant: Massachusetts Institute of Technology, Cambridge, MA (US)

(72) Inventors: Hugh M. Herr, Concord, NH (US); Hyungeun Song, Cambridge, MA (US); Shriya Sruthi Srinivasan, Strongsville, OH (US)

(73) Assignee: Massachusetts Institute of Technology, Cambridge, MA (US)

( * ) Notice: Subject to any disclaimer, the term of this patent is extended or adjusted under 35 U.S.C. 154(b) by 961 days.

(21) Appl. No.: 17/759,219

(22) PCT Filed: Jan. 21, 2021

(86) PCT No.: PCT/US2021/014355
§ 371 (c)(1),
(2) Date: Jul. 21, 2022

(87) PCT Pub. No.: WO2021/150709
PCT Pub. Date: Jul. 29, 2021

(65) Prior Publication Data
US 2023/0050411 A1 Feb. 16, 2023

Related U.S. Application Data

(60) Provisional application No. 63/029,137, filed on May 22, 2020, provisional application No. 62/965,002, filed on Jan. 23, 2020.

(51) Int. Cl.
A61F 2/68 (2006.01)
A61F 2/50 (2006.01)

(52) U.S. Cl.
CPC ........ A61F 2/68 (2013.01); A61F 2002/5061 (2013.01); A61F 2002/5066 (2013.01); A61F 2002/6827 (2013.01)

(58) Field of Classification Search
CPC .............................................. A61F 2002/6827
See application file for complete search history.

(56) References Cited

U.S. PATENT DOCUMENTS 9,474,634 B2 * 10/2016 Herr .......................... A61F 2/72
10,898,351 B2 * 1/2021 Herr .......................... A61F 2/68
(Continued)

FOREIGN PATENT DOCUMENTS

DE 102007013660 A1 9/2008
WO WO-2015061453 A1 * 4/2015 ......... A61N 1/36003
(Continued)

OTHER PUBLICATIONS

Mablekos-Alexiou et al., "A biomechatronic Extended Physiological Proprioception (EPP) controller for upper-limb prostheses," In 2015 IEEE/RSJ International Conference on Intelligent Robots and Systems (IROS), Sep. 28, 2015, pp. 6173-6178.
(Continued)

*Primary Examiner* — Jacqueline Woznicki
(74) *Attorney, Agent, or Firm* — Hamilton, Brook, Smith & Reynolds, P.C.

(57) ABSTRACT

Mechanoneural Interfaces (MIs) and methods of forming MIs are provided, including cutaneous mechanoneural interfaces (CMIs) and proprioceptive mechanoneural interfaces (PMIs). A CMI includes a device in operative arrangement with a muscle actuator to stimulate muscle contraction, the muscle actuator disposed in a substantially circumferential configuration about a skin flap that includes a native or regenerative neurovascular structure of an amputated body segment. A PMI includes an actuator mechanically linked to a muscle end organ and configured to apply a force to the muscle end organ, the actuator including a synthetic actuator or a biological muscle actuator. The muscle end organ is of an agonist-antagonist muscle pair and can include at least one of a native or regenerative neurovascular structure.
(Continued)

CMIs and PMIs can each further include a controller configured to provide a stimulation signal or operate an actuator based on a signal received from a sensor of a prosthetic device.

10 Claims, 22 Drawing Sheets

(56)            References Cited

U.S. PATENT DOCUMENTS

| | | |
|---|---|---|
| 12,245,956 B2 * | 3/2025 | Herr .................... A61N 1/36003 |
| 2007/0038311 A1 * | 2/2007 | Kuiken ...................... A61F 2/72 |
| | | 623/24 |
| 2008/0228240 A1 | 9/2008 | Edell et al. |
| 2012/0101595 A1 | 4/2012 | Jung et al. |
| 2015/0173918 A1 | 6/2015 | Herr et al. |
| 2015/0265430 A1 | 9/2015 | Branemark et al. |
| 2016/0143751 A1 | 5/2016 | Chestek et al. |
| 2017/0120484 A1 * | 5/2017 | Farris .................... B29C 64/182 |

FOREIGN PATENT DOCUMENTS

| | | | |
|---|---|---|---|
| WO | WO-2017120484 A1 * | 7/2017 | ......... A61N 1/36003 |
| WO | WO-2018085253 A1 * | 5/2018 | ........... A61K 9/0009 |

OTHER PUBLICATIONS

International Search Report and Written Opinion for International Application No. PCT/US2021/014355, entitled "Mechanoneural Interfaces for Prosthetic Control." Date Mailed: Jul. 12, 2021.

* cited by examiner

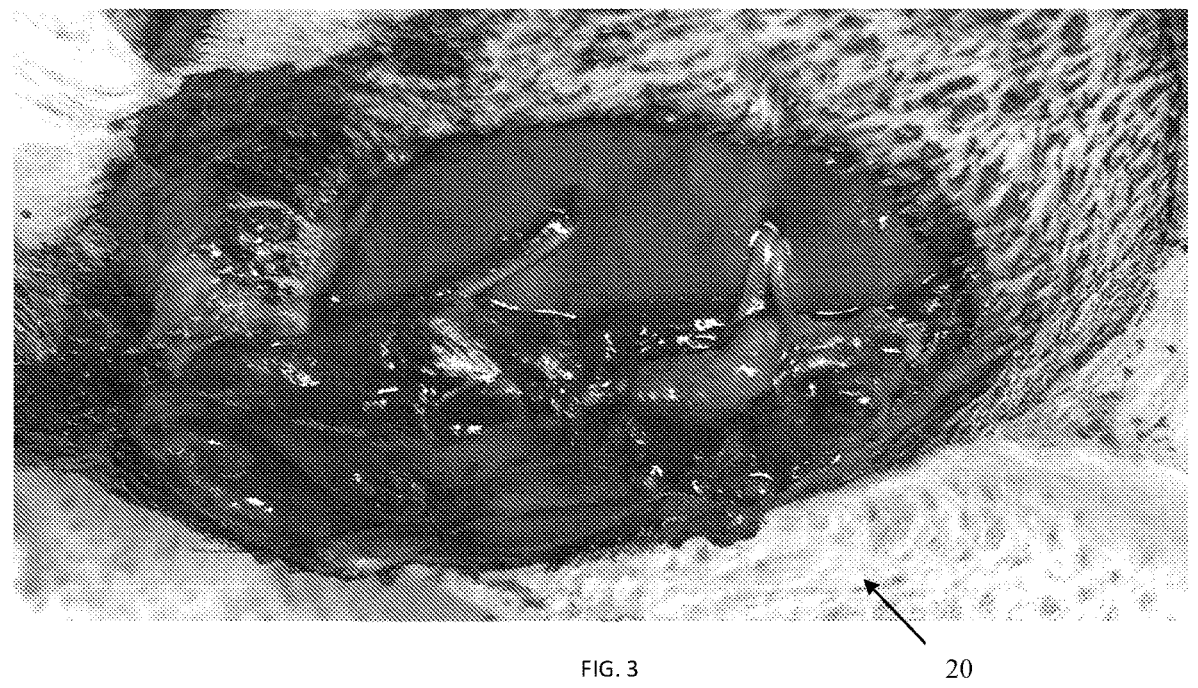
FIG. 3                                    20
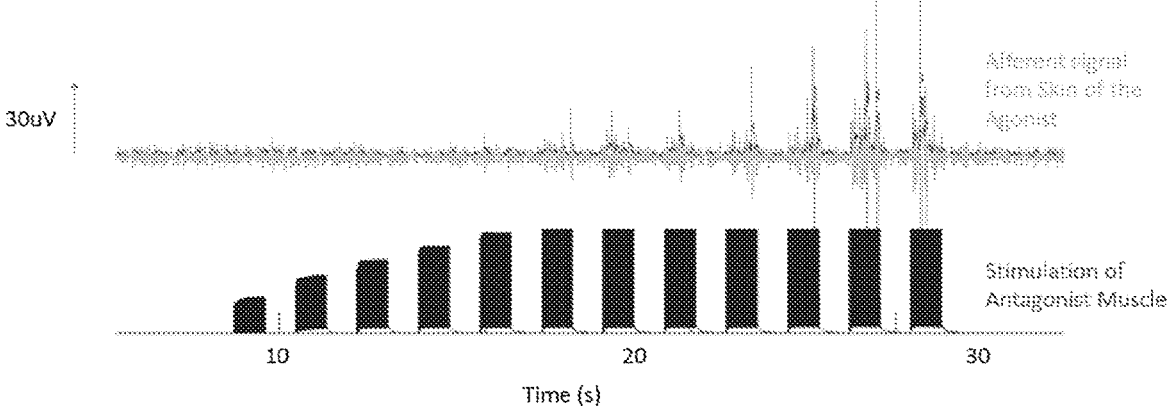
FIG. 4

313

315

D

Total Afferent Signal

RA Receptor Signal

SA Receptor Signal

Muscle Actuation

1s

C

Rectified Afferent Signal

Raw Afferent Signal

Muscle Actuation 2.5s

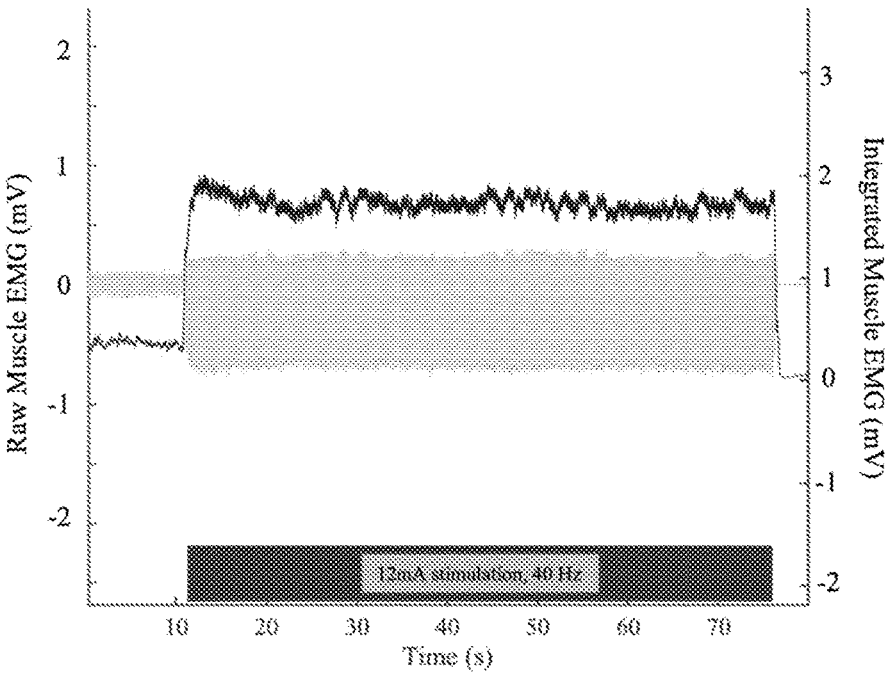
FIG. 13
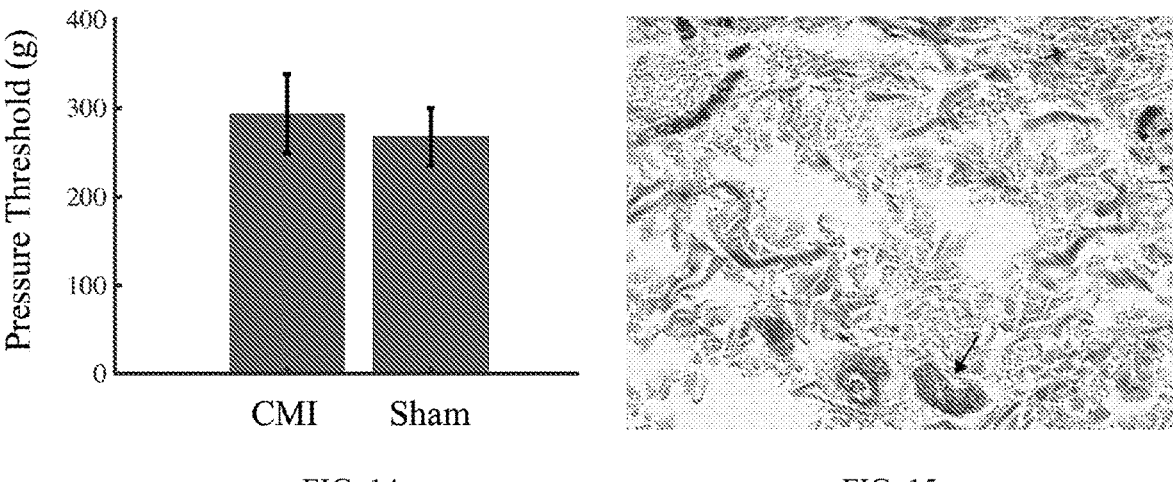
FIG. 14
FIG. 15

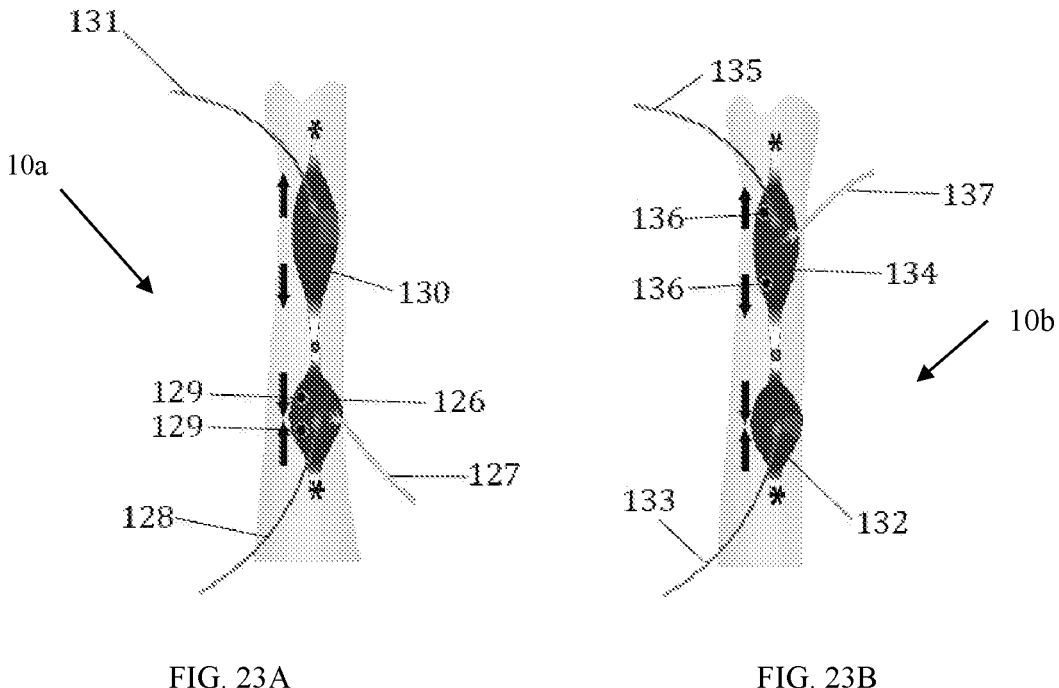
FIG. 23A                                    FIG. 23B
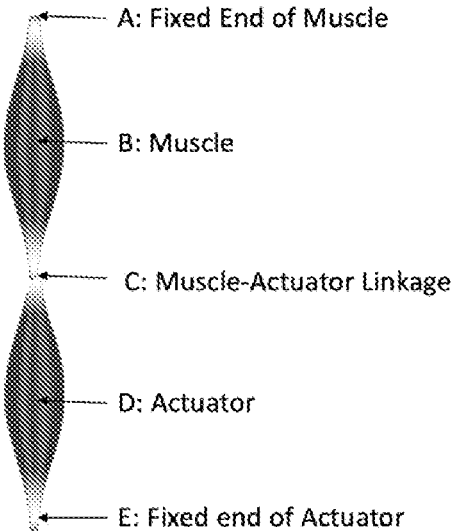
A: Fixed End of Muscle
B: Muscle
C: Muscle-Actuator Linkage
D: Actuator
E: Fixed end of Actuator
FIG. 24

500

550

MECHANONEURAL INTERFACES FOR PROSTHETIC CONTROL

RELATED APPLICATIONS

This application is the U.S. National Stage of International Application No. PCT/US2021/014355, filed Jan. 21, 2021, which designates the U.S., published in English, and claims the benefit of U.S. Provisional Application No. 62/965,002, filed Jan. 23, 2020 and U.S. Provisional Application No. 63/029,137, filed on May 22, 2020. The entire teachings of the above applications are incorporated herein by reference.

BACKGROUND

Cutaneous sensation plays a central role in our cognitive, emotional, developmental, and behavioral processes. As a multifunctional medium of exteroception, communication and protection, the skin utilizes specialized receptors (contact, pressure, shear, pain, vibration, and temperature) to create an intricate ensemble of distinct signals that are virtuously integrated by the peripheral nervous system. The resulting afferent feedback provides humans a sense of touch critical to tactile sensation, balance, motor and postural control, as well as grip and manipulation of objects.

The fundamental motor unit to control a biological joint is an agonist-antagonist muscle-tendon pair. Such a muscle-tendon relationship allows organisms to simultaneously control joint state (position and speed) and impedance (stiffness and damping) for upper and lower extremity motor tasks. Golgi tendon organs of agonist muscles and muscle spindle receptors that are known to discharge when a muscle is passively elongated, but which stop firing abruptly whenever that muscle is slackened passively, provide for proprioception of one's joint or limb state.

Standard-of-care prosthetic systems focus primarily on restoring the mechanical components of an extremity with little to no neural control and no cutaneous and proprioceptive feedback. Thus, patients experience a significant reduction in their sensory experience and motor function; for example, persons with upper-extremity amputation are often incapable of fine motor tasks such as buttoning a shirt. The decrease in functionality often results in a diminutive association of the prosthesis with their body, psychosocial distress, and device abandonment. A growing body of evidence demonstrates the positive influence of neuroprosthetic sensory feedback in increasing confidence, mobility, functionality, and decreasing mental and physical fatigue. Thus, there is an unmet clinical need to design methodologies to restore proprioceptive and cutaneous sensations in a neuroprosthetic system following amputation.

SUMMARY

Methods and systems relating to muscle-activated interfaces that can be used to supply neuroprosthetic cutaneous feedback or neuroprosthetic proprioceptive feedback are provided. The methods and systems can be used to restore at least partial sensory function of a limb of an individual, for example to simulate cutaneous sensory feedback, proprioceptive sensory feedback, or both.

A method of providing cutaneous neuroprosthetic feedback includes stimulating a muscle based on a signal received from a sensor of a prosthetic device where the muscle is mechanically disposed about a skin flap comprising at least one of a native or regenerative neurovascular structure of an amputated body segment.

Stimulating the muscle disposed about the skin flap can include causing a strain to be applied to the skin flap, causing vibration of the skin flap, causing sliding of the skin flap relative to the muscle, causing constriction or compression of the skin flap, or any combination thereof. Stimulation of the muscle can cause at least two of the following to occur simultaneously: application of strain to the skin flap, vibration of the skin flap, sliding of the skin flap relative to the muscle, constriction of the skin flap, and compression of the skin flap. Graded touch sensations, vibration sensations, or both touch and vibration sensations can be generated at the skin flap.

The muscle can be disposed in a substantially circumferential configuration about the skin flap. For example, the muscle can be disposed in a cuffed configuration or a conical configuration relative to the skin flap. The muscle can be partially circumferentially disposed about the skin flap.

A signal received from the sensor of the prosthetic device can include at least one of pressure, shear, stress, strain, and vibration information detected at a surface of the prosthetic device, or any combination thereof.

The native or regenerative neurovascular structure can include at least one mechanoreceptor selected from the group consisting of Meissner corpuscles, Pacinian corpuscles, Ruffini corpuscles, Merkel cells, and free nerve endings.

A method of restoring at least partial sensory function of a limb of an individual includes surgically removing a patch of skin from a body segment of the limb and translocating the patch of skin to form a skin flap at a non-anatomical portion of the individual. The method further includes disposing a muscle mechanically in combination with the skin flap and disposing an output device at or near the muscle. The skin flap includes at least one of a native or regenerative neurovascular structure. Electrical or optical signals can be transmitted by the output device to cause contractions of the muscle about the skin flap to thereby cause a skin flap strain and a neural cutaneous afferent signal to restore at least partial sensory function of the limb.

The method of restoring at least partial sensory function can further include connecting the output device to a sensory controller of a prosthetic device and connecting the sensory controller to a sensor disposed at the prosthetic device. The sensor can be configured to detect application of at least one of pressure, shear, stress, strain, and vibration at the prosthetic device. The controller can be configured to stimulate the muscle via the output device upon detection of at least one of pressure, shear, stress, strain, and vibration by the sensor. Stimulation of the muscle by the controller can include, for example, generating a graded touch sensation at the skin flap, generating a vibration sensation at the skin flap, or generating a combination thereof.

A method of simulating proprioceptive sensory feedback includes mechanically linking at least one pair of agonist and antagonist muscles and surgically removing at least two patches of skin from a body segment of an individual. The method further includes translocating the at least two patches of skin to the at least one pair of agonist and antagonist muscles, one of the at least two patches of skin associated with the agonist muscle and the other of the at least two patches of skin associated with the antagonist muscle, and disposing at least one device at or near the at least one pair of agonist and antagonist muscles. Each patch of skin and each muscle includes at least one of a native or regenerative neurovascular structure. Signals can be transmitted to the at least one device to stimulate at least one of the agonist and antagonist muscles, thereby simulating proprioceptive feedback.

The method of simulating proprioceptive sensory feedback can further include connecting the at least one device to a motor controller of a prosthetic device, the motor controller configured to stimulate the at least one of the agonist and antagonist muscles via the at least one device based upon a change in position or orientation of the prosthetic device. The device can be further configured to detect an electromyography signal from the at least one pair of agonist and antagonist muscles, and the motor controller can be further configured to provide a change in position or orientation of the prosthetic device based on a detected electromyography signal.

In any of the methods, the body segment can be, for example, a hand or foot of the individual. The native or regenerative neurovascular structure of the skin flap can include at least one mechanoreceptor selected from the group consisting of Meissner corpuscles, Pacinian corpuscles, Ruffini corpuscles, Merkel cells, and free nerve endings. The muscle can be, for example, a muscle graft.

The device or output device can be, for example, an electrode, a light source, or a combination thereof. The light source can be, for example, a transdermal light source capable of stimulating an optogenetically transduced nerve of the muscle. Examples of stimulation devices and methods suitable for use with embodiments of the present invention are further described in International Publication No. WO2018/085253, entitled "Transdermal Optogenetic Peripheral Nerve Stimulation," and International Publication No. WO2017/120484, entitled "Method and System For Providing Proprioceptive Feedback And Functionality Mitigating Limb Pathology," the entire teachings of which are incorporated herein by reference.

A cutaneous mechanoneural interface (CMI) includes a device in operative arrangement with a muscle actuator to stimulate muscle contraction and a controller configured to provide a stimulation signal to the device based on a signal received from a sensor of a prosthetic device. The muscle actuator is disposed in a substantially circumferential configuration about a skin flap that comprises at least one of a native or regenerative neurovascular structure of an amputated body segment.

The stimulation signal can provide for any of a strain sensation, a vibratory sensation, a sliding sensation, and constriction or compression at the skin flap by the muscle actuator, including any combination thereof and any simultaneous combination thereof. The stimulation signal can provide for a graded touch sensation at the skin flap by the muscle actuator.

The muscle actuator can be disposed about the skin flap in any substantially circumferential arrangement, for example, in a cuffed configuration or in a conical configuration.

The signal received from the sensor of the prosthetic device can include at least one of pressure, shear, stress, strain, and vibration information detected at a surface of the prosthetic device. The device in operative arrangement with the muscle actuator can be, for example, an electrode. The muscle actuator can be a muscle graft.

An agonist-antagonist dermal interface includes at least one output device disposed at or near at least one of an agonist muscle graft and an antagonist muscle graft. For example, the at least one output device can be in operative arrangement with at least one of the agonist muscle graft and the antagonist muscle graft to stimulate muscle contraction.

Alternatively, or in addition, the at least one output device can be configured to detect an electromyography signal. A controller is configured to provide a signal to the at least one output device or detect a signal from the at least output device. For example, the controller can be configured to provide a stimulation signal to the at least one device based on a signal received from a sensor of a prosthetic device. Alternatively, or in addition, the controller can be configured to detect a state or change in state of at least one of the muscle grafts, such as detecting an electromyography signal. The agonist and antagonist muscle grafts are mechanically linked, and a translocated skin patch is disposed at each of the agonist muscle graft and antagonist muscle graft. Each patch of skin and each muscle includes at least one of a native or regenerative neurovascular structure, such that, upon stimulation by the device, proprioceptive sensory feedback is simulated.

The signal received from the sensor of the prosthetic device can indicate a change in position or orientation of the prosthetic device. The device in operative arrangement with at least one of an agonist muscle graft and an antagonist muscle graft can be further configured to detect an electromyography signal, and the controller can be further configured to provide a change in position or orientation of the prosthetic device based on a detected electromyography signal.

A method for simulating proprioceptive sensory feedback includes mechanically linking a muscle end organ to an actuator configured to apply a force to the muscle end organ and. The actuator comprises a synthetic actuator or a biological muscle actuator, such as a biological muscle actuator that is denervated or that is innervated with a cutaneous nerve. The muscle end organ is one of an agonist-antagonist muscle pair and comprises at least one of a native or regenerative neurovascular structure. The controller, with the actuator, is configured to actuate the muscle end organ independently of the other of the agonist-antagonist muscle pair based on a signal received from a sensor of a prosthetic device, thereby simulating proprioceptive sensory feedback.

A proprioceptive mechanoneural interface (PMI) includes an actuator mechanically linked to a muscle end organ and configured to apply a force to the muscle end organ and a controller. The actuator comprises a synthetic actuator or a biological muscle actuator, such as a biological muscle actuator that is denervated or that is innervated with a cutaneous nerve. The muscle end organ is one of an agonist-antagonist muscle pair and comprises at least one of a native or regenerative neurovascular structure. The controller is configured to operate the actuator based on a signal received from a sensor of a prosthetic device, the controller providing for actuation of the muscle end organ independent of the other of the agonist-antagonist muscle pair, thereby simulating proprioceptive sensory feedback.

The actuator can be implanted within a body segment that includes the muscle end organ. Mechanical linking of the muscle end organ to the actuator can be by formation of a passive material connection with a tendon, a ligament, fascia, a biocompatible artificial material, or any combination thereof. Where the actuator is a muscle, such as a muscle graft, the muscle can be denervated or can be innervated with a cutaneous nerve. Where the actuator is a synthetic actuator, the actuator can include an electrically-active polymer, a pneumatic artificial muscle, or a hydraulic artificial muscle. The actuator can be disposed externally of the body segment comprising the muscle end organ, with mechanical linking of the muscle end organ to the actuator being by cineplasty.

A device can be disposed at the muscle end organ and configured to sense a state, change in state, or activation level of the muscle end organ. For example, the device can be or include an electrode configured to sense an electro-myography signal, and the device can be or include one or more implants configured to detect muscle fascicle length, speed, or combination thereof.

A proprioceptive mechanoneural interface system includes at least two proprioceptive mechanoneural inter-faces (PMIs) and a controller configured to operate the actuators of the PMIs based on a signal received from a sensor of a prosthetic device, the controller providing for independent actuation of each PMI.

A mechanoneural interface system includes at least one cutaneous mechanoneural interface (CMI), at least two proprioceptive mechanoneural interfaces (PMIs), and a con-troller configured to operate the CMI and PMIs based on a signal received from a sensor of a prosthetic device to provide afferent cutaneous and proprioceptive feedback, the controller providing for independent actuation of each PMI.

Each PMI can include at least one device disposed at the muscle end organ and configured to sense a state, change in state, or activation level of the muscle end organ, and the controller can be further configured to provide efferent control of the prosthetic device. For example, the controller can be configured to determine a target action and reaction of the prosthetic device based on a virtual limb model, and, optionally, determine an error in target action and reaction of the prosthetic device based on the virtual limb model and provide for adjusted actuation of the PMIs.

The controller can be configured to determine a target sensory activity based on a cutaneous sensory map. For example, the device of each CMI can be further configured to sense a state or change in state of the muscle actuator, and the controller can be configured to determine an error in target sensory activity and reaction of the muscle actuator based on the cutaneous sensory map.

BRIEF DESCRIPTION OF THE DRAWINGS

The foregoing will be apparent from the following more particular description of example embodiments, as illus-trated in the accompanying drawings in which like reference characters refer to the same parts throughout the different views. The drawings are not necessarily to scale, emphasis instead being placed upon illustrating embodiments.

FIG. 3 is a photo of an ADI provided in a murine model.

FIG. 4 is a graph of results obtained from the ADI of the murine model shown in FIG. 3. The graph includes mea-sured afferent signals (top section of graph) generated at a skin patch associated with the agonist muscle based on stimulation (bottom section of graph) provided to the asso-ciated antagonist muscle.

FIG. 5A illustrates stimu-lation of the CMI and example communication with a sensorized prosthesis. FIG. 5B is a schematic illustration of the CMI.

FIG. 6A is a photo and schematic of isolation of a skin flap. FIG. 6B is a photo and schematic of isolation of an extensor digitorus longus (EDL) muscle from an anterior compartment along with two blood vessels. FIG. 6C is a photo and schematic of circumferential wrapping of the skin flap around the muscle. FIG. 6D is a photo and schematic of an attachment of an electrode to the epimysium of the muscle for stimulation. FIG. 6E is a graph illustrating EMG response of stimulation of muscle grafts over time. Tissue remodeling at 6 weeks demonstrated a composite architecture with efficacious actuator tension and transverse striations. FIG. 6F is a graph illustrating electrical stimulation (lower bar graph) of the muscle actuator and corresponding generated average maximal forces (solid curve) and peak forces (dots). The scale bar of FIGS. 6A-6D is 1 cm. The bars of FIG. 6F represent standard deviations.

FIG. 7A is a graph illustrating graded afferent neural responses produced by the CMI (purple line) and contralateral skin (control, red line). Normalized values to maximum electroneurographic signal (ENG) are shown. Receptor saturation is indicated by plateaus between 3 mm and 4 mm and greater than 5 mm in the CMI. FIG. 7B is a graph illustrating graded afferent response of electrical stimulation of the CMI. Between 3-4 mA and beyond 10 mA, actuation saturated receptors. FIG. 7C is a graph illustrating actuation results. A representative trial of muscle actuation demonstrates growth in raw and rectified afferent signal strength. Once muscle is mechanically uncoupled, no afferent signals are generated. FIG. 7D is a graph illustrating actuation results. Patterned stimulation demonstrated dis-tinct rapidly adapting (RA) and slowly adapting (SA) affer-ent responses from different fine wire electrodes during the same stimulation trial. The total signal demonstrates the capacity for the CMI to detect and integrate static touch and vibratory sensations. The bars of FIGS. 7A and 7B represent standard deviations.

FIG. 8A is a graph illus-trating muscular vibration produced afferent responses in the CMI that were 1:1 phase locked with the vibration pattern for frequencies of 0.5-80 Hz. FIG. 8B is a graph illustrating spectral information demonstrating distinct afferents from each mode of vibration.

FIG. 9A is an image of a cross section of the CMI demonstrating muscle actuator cuffed around a skin flip (skin flap outlined in black dotted line). FIG. 9B is an image of fibers of the muscle actuator that are largely oriented in a longitudinal fashion around the skin flap, enabling effica-cious actuation. FIG. 9C is an image of hematoxylin and eosin staining of a CMI cross-section, which demonstrates multiple healthy cutaneous nerves found in the skin flap of the CMI. The variety in size supports the range of afferent responses measured. FIG. 9D is an image of the interface between muscle and skin tissues, which shows the strongly embedded nature of the skin flap and adhesion at the interface. FIG. 9E is an image of immunohistochemical staining with s100 revealed numerous Merkel cells in the dermal layer. FIG. 9F is an image illustrating Meissner corpuscles found in the deeper layers of the CMI, providing a structural basis for vibratory sensation. FIG. 9G is an image of trichrome staining, which shows healthy myocytes lined by dense collagenous tissue at the interface of the muscular actuator and skin.

FIG. 13 is a graph of fatigue response results of a murine model CMI under sustained stimulation. Following 15 minutes of stimulation tests, 40 Hz stimulation inducing tetanic contraction was applied to the muscle graft. Output force from a representative trial demonstrates less than a 5% decrease over the course of 65 seconds.

FIG. 14 is a graph of nociceptive sensitivity threshold results. The nociceptive threshold to mechanical pressure was tested by the use of calibrated forceps on groups (n=5) with CMI's and sham surgery. Average and standard deviations for each group are presented. No significant difference was found in the sensitivity between groups (p<0.69, 2-tailed t-test).

FIG. 15 is an image illustrating cutaneous nerves in a murine model CMI. Luxol fast blue staining demonstrates small cutaneous nerves innervating the skin flap of the CMI, as indicated by the black arrow.

FIG. 16A is an image and schematic of a muscle that is sutured to the dermal surface to induce contraction and extension of the skin in response to muscular actuation. FIG. 16B is an image and schematic of a pedicled skin flap that is sandwiched between muscle and fascia. Contraction of the muscle induces a constriction of the skin flap, producing sensations of static touch. FIG. 16C is an image and schematic of a muscle fashioned around a skin flap in a conical architecture such that muscular actuation causes constriction and sliding of the skin flap out of the conical pocket. This can activate both Merkel cells and Meissner corpuscles to sense touch and sliding across the surface of the skin. In each case, cutaneous receptors can be produced by native receptors and communicated through native cutaneous nerves.

FIGS. 23A-23B are schematics of PMIs, with FIG. 23A illustrating a flexion PMI and FIG. 23B illustrating an extension PMI.

FIG. 24 is a diagram of a PMI constructed with a muscle actuator.

DETAILED DESCRIPTION

A description of example embodiments follows.

Agonist-Antagonist Dermal Interfaces (ADIs)

Figures 1, 2:
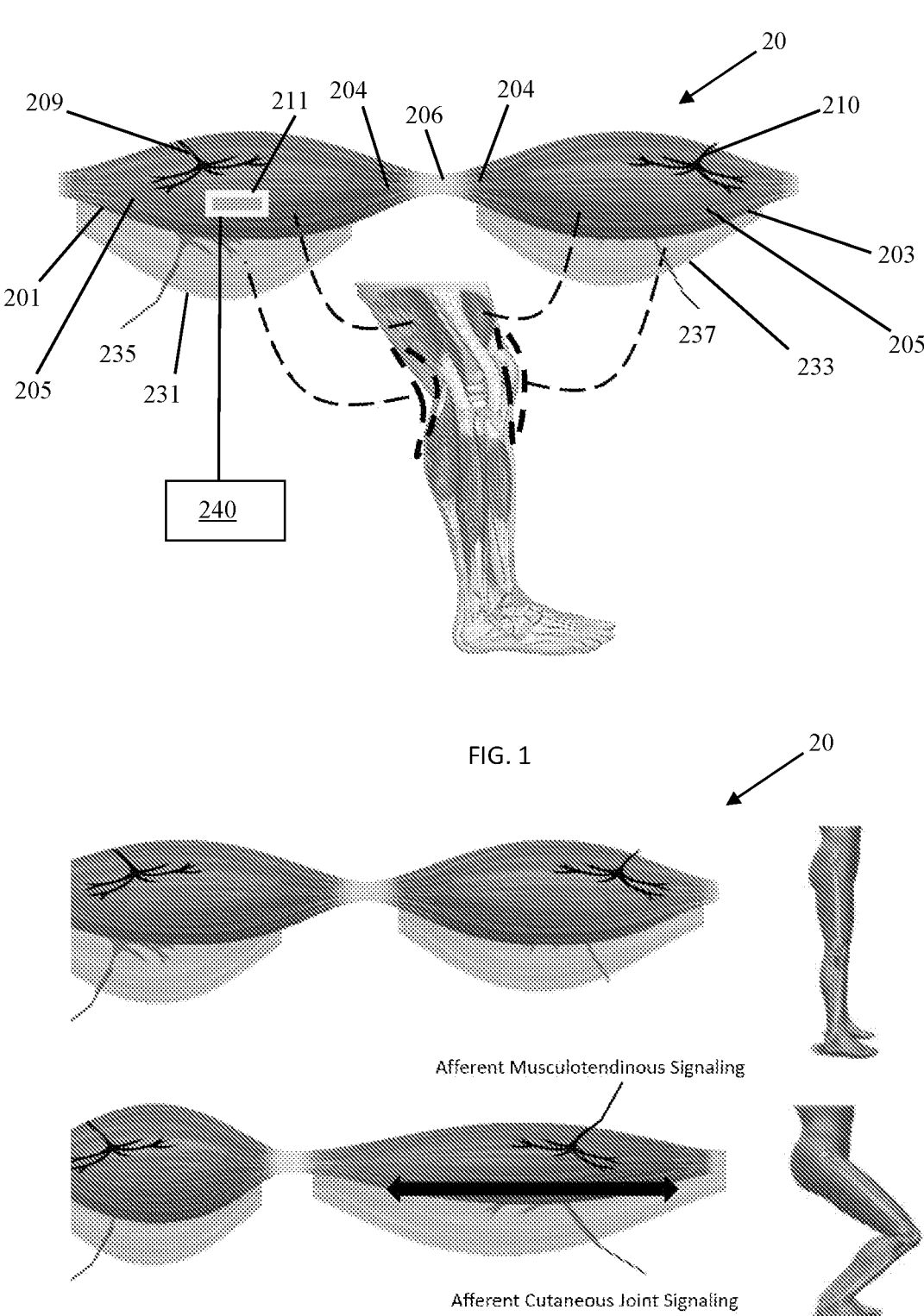
FIG. 1 illustrates an example of an agonist-antagonist dermal interface (ADI).
FIG. 2 illustrates an example of afferent cutaneous joint signaling of the ADI of FIG. 1.

An example of an agonist-antagonist dermal interface (ADI) is shown in FIG. 1. The interface 20 includes at least two muscle grafts 200, 201 arranged in an agonist-antagonist pairing. As illustrated, the muscle grafts 200, 201 are mechanically linked by a link 206, such as by suturing of tendons. The muscle grafts 200, 201 can include their respective native Golgi tendon organs 204 and intrafusal muscle spindle stretch fibers 205.

The interface 20 further includes at least two translocated skin patches 231, 233, each translocated skin patch disposed at one of the agonist and antagonist muscle grafts. As used herein, the term "disposed at" (e.g., a first component "disposed at" a second component) means that the components are in operable proximity. For example, a skin patch "disposed at" a muscle graft may be in contact with the muscle graft, attached to the muscle graft, fixed with respect to the muscle graft, or otherwise connected to the muscle graft.

Each of the muscle grafts 200, 201 and skin patches 231, 233 includes at least one of a native or regenerative neurovascular structure. For example, each of the muscle grafts 200, 201 includes a motor nerve 209, 210, and each of the skin patches 231, 233 includes a sensory nerve 235, 237. At least one device 211, such as an electrode, is in operative arrangement with at least one of the muscle grafts to stimulate muscle contraction. The interface further includes a controller 240 configured to provide a stimulation signal to the device 211. The stimulation signal can be based on a signal received from a sensor of a prosthetic device (e.g., device 455 in FIG. 10).

The agonist-antagonist dermal interface can provide for more realistic proprioception through its inclusion of translocated skin patches disposed at each of the muscle grafts. The translocated skin patches provide for a dermal interface at each muscle of an agonist-antagonist pair and can enable cutaneous signaling associated with an agonist-antagonist movement. For example, as illustrated in FIGS. 1 and 2, the agonist-antagonist dermal interface can mimic proprioception of knee bending for a lower-limb amputee, with afferent musculotendinous signaling provided by the antagonist muscle graft 201 and afferent cutaneous joint signaling provided by the skin patch 233 associated with the antagonist muscle graft. In particular, to mimic proprioception of knee bending, a signal is provided by controller 240 to electrode 211 to stimulate contraction of the agonist muscle graft 200. While FIG. 1 illustrates an electrode disposed only at one of the two muscle grafts, electrodes may be disposed at each of the muscle drafts. The electrodes can be used by the controller 240 to either sense electromyography (EMG) signals from the subject and/or to electrically stimulate the muscle grafts 201, 203.

A method for simulating proprioceptive sensory feedback includes mechanically linking at least one pair of agonist and antagonist muscles, surgically removing at least two patches of skin from a body segment of an individual, and translocating the at least two patches of skin to the pair of agonist and antagonist muscles such that each muscle has an associated skin patch. The method can further include disposing a device, such as an electrode, at or near at least of the agonist and antagonist muscles such that signals can be transmitted to the device to stimulate a contraction and thereby simulate proprioceptive feedback.

The agonist and antagonist muscles and/or associated skin patches can be dissected from an amputated portion of a limb together and disposed at a non-anatomical portion of the individual. As used herein, the term "non-anatomical portion" is a location that is not a natural anatomical location for the tissue. For example, if a foot muscle is translocated up the leg to the thigh, it can be stated that the muscle was inserted into a non-anatomical portion of the individual. The agonist and antagonist muscles and/or associated skin patches can be dissected with their native innervation or can include new regenerative innervation.

Additional examples of simulating cutaneous and proprioceptive feedback are further described in U.S. Pat. No. 9,474,634, entitled "Peripheral Neural Interface Via Nerve Regeneration to Distal Tissues," the entire teachings of which are incorporated herein by reference.

A murine model of an agonist-antagonist dermal interface and testing results associated therewith are shown in FIGS. 3 and 4 and further described in Example 2 herein.

Mechanoneural Interfaces (MIs)

A Mechanoneural Interface (MI) is a synthetic-biologic interface for linking a human peripheral nerve to wearable machines, such as prostheses, orthoses and exoskeletons. In this framework, a state and load applied to a tissue end organ, such as skin or muscle, is computer controlled to modulate the mechanoneural transduction into the central nervous system (CNS). Through artificially controlled actuation, the length, speed and force of an end organ can be independently controlled via control targets derived from a Virtual Limb Model (VLM). For sensory feedback, control targets can be derived from a Cutaneous Sensory Map (CSM). The VLM comprises a digital model of the relevant biological appendage that is to be emulated through prosthetic intervention. The CSM comprises a digital model of relevant sensory paradigms, such as force, strain, sensation (e.g., vibration, graded touch, etc.). Two types of MIs are further described herein, namely a Cutaneous Mechanoneural Interface (CMI) and a Proprioceptive Mechanoneural Interface (PMI). A Mechanoneural Interface Controller (MIC) can modulate efferent/afferent signaling between the MIs and the prosthetic appliance.

As used herein, the term "end organ" is a tissue body (e.g., a muscle or a skin patch) that is innervated (e.g., includes native and/or regenerative nerve structure) and that is acted upon by an actuator. The actuator applies computer-controlled strains, strain rates, and loads upon the end organ for the purpose of directly controlling the state of the end organ, and thereby mechanoneural transduction into the central nervous system (CNS). Each end organ that is to be represented by a control system can have an independent actuator so as to provide transduction signaling into the CNS that is independent of each other end organ construct represented by the system, enabling natural afferent signaling from the prosthesis into the CNS.

An "actuator" of an MI can include synthetic actuators or biological muscle actuators. As used herein a "muscle actuator" or a "biological "muscle actuator" is a muscular body that lacks a native nerve structure (i.e., motor nerves). For example, a muscle actuator can include a denervated muscle or a muscle that has been innervated with a cutaneous nerve. Muscle innervation with a cutaneous nerve can advantageously provide for enhanced viability of the muscle, as further described in Nghiem et al., "Sensory protection to enhance functional recovery following proximal nerve injuries: current trends" Plast Aesthet Res; Vol 2; Issue 4; Jul. 15, 2015, the entire contents of which is incorporated herein by reference.

As used herein a "synthetic actuator" is an actuator that consists of, or substantially comprises, non-biological structures. Examples of suitable synthetic actuators include an electrically-active polymer, a pneumatic artificial muscle, and a hydraulic artificial muscle.

Cutaneous Mechanoneural Interfaces (CMIs)

The current amputation paradigm typically destroys sensory end organs and provides no anatomical interface for cutaneous neuroprosthetic feedback. Cutaneous Mechanoneural Interfaces (CMIs) are provided. CMIs can provide an afferent neural platform and comprise a muscle actuator coupled to a natively or regeneratively-pedicled skin flap in, for example, a cuff-like architecture. Through neuroprosthetic electrical stimulation, the muscle can be actuated to induce strains or oscillatory vibrations on the skin flap, proportional to a contact pressure measured by prosthetic sensors. Natural dermal mechanotransducers can generate the corresponding afferent signals, enabling a more genuine sensory experience for the prosthetic user.

Evaluation of the biomechanical and electrophysiological capacities of the CMI in a murine model were performed and is further described in Example 1 in the Exemplification section herein. The CMI successfully elicits at least four levels of graded contact and eight distinct vibratory afferents that are insignificantly different from the analogous mechanical stimulation of intact skin. Various modes of CMI actuation exhibit the ability to independently engage slowly-adapting and rapidly adapting mechanotransducers and establish the capacity for the CMI to recreate an array of cutaneous sensations.

Figures 5A, 5B:
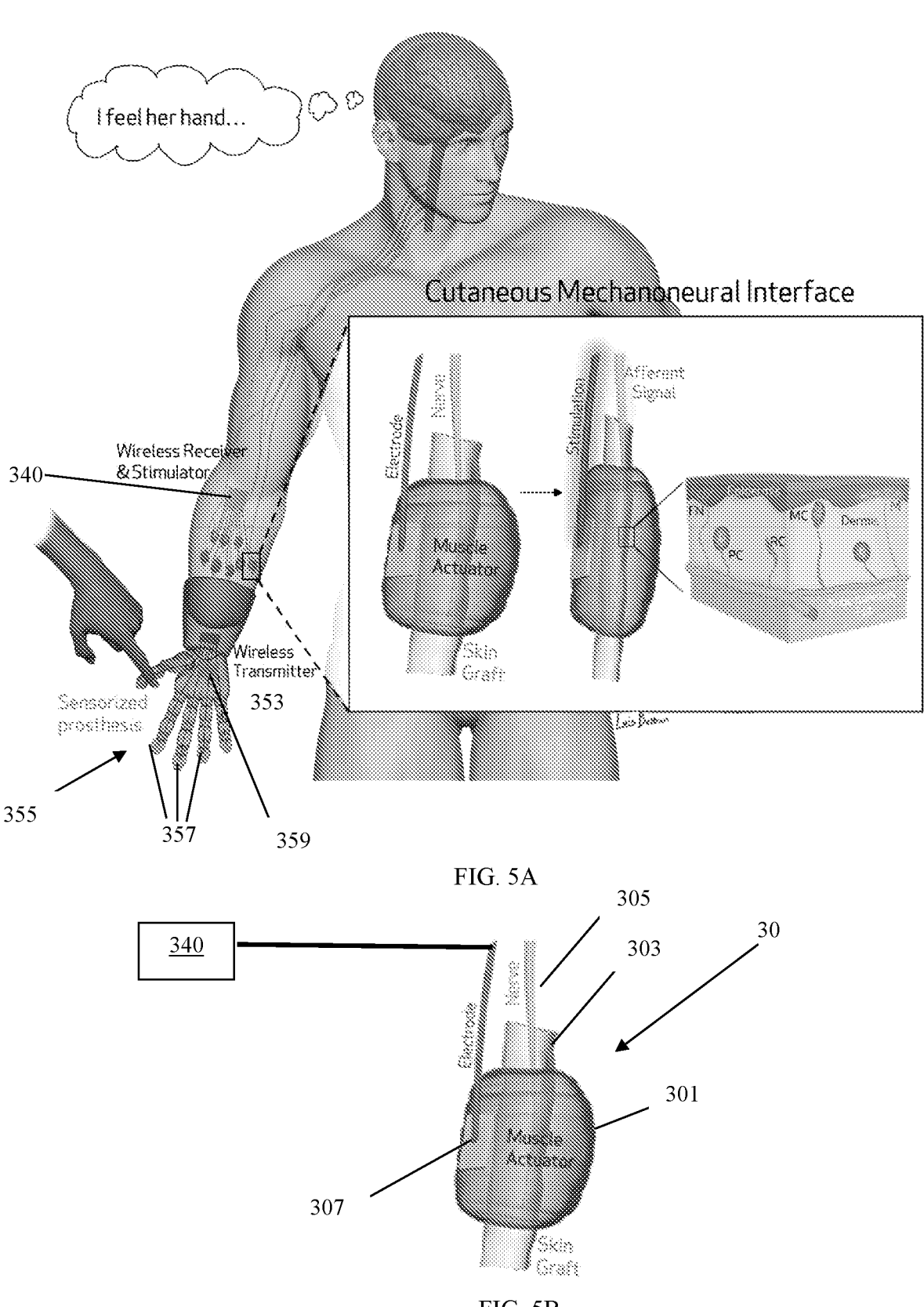
FIGS. 5A and 5B illustrate an example of a cutaneous mechanoneural interface (CMI).
Figure 16A:
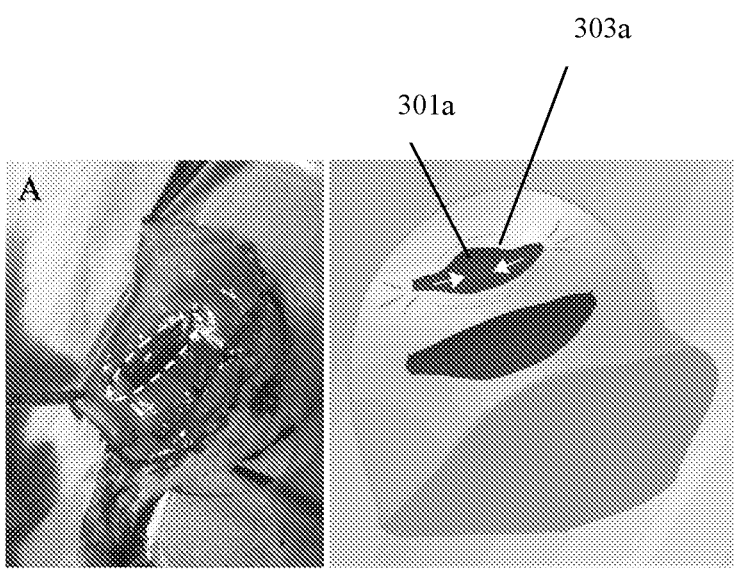
FIGS. 16A-16C illustrate examples of alternative CMI architectures.
Figure 16B:
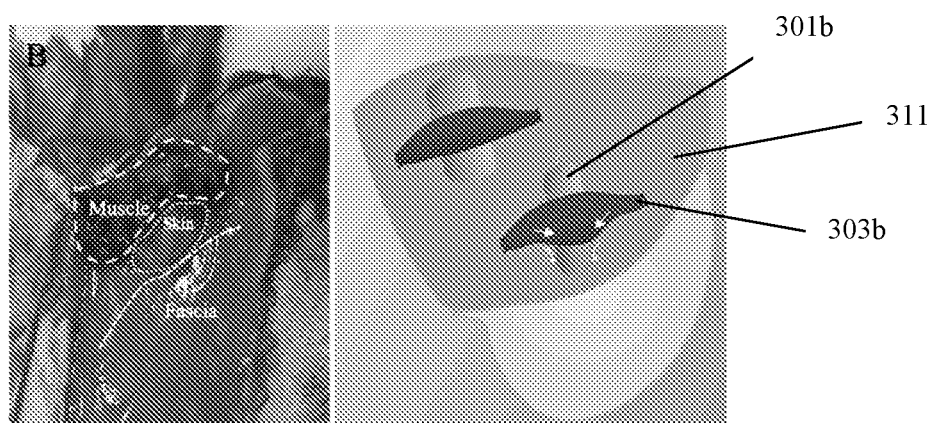
Figure 16C:
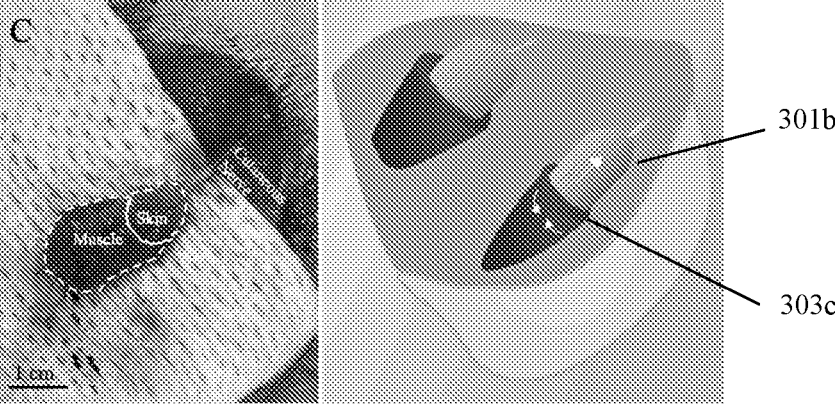
Figure 17:
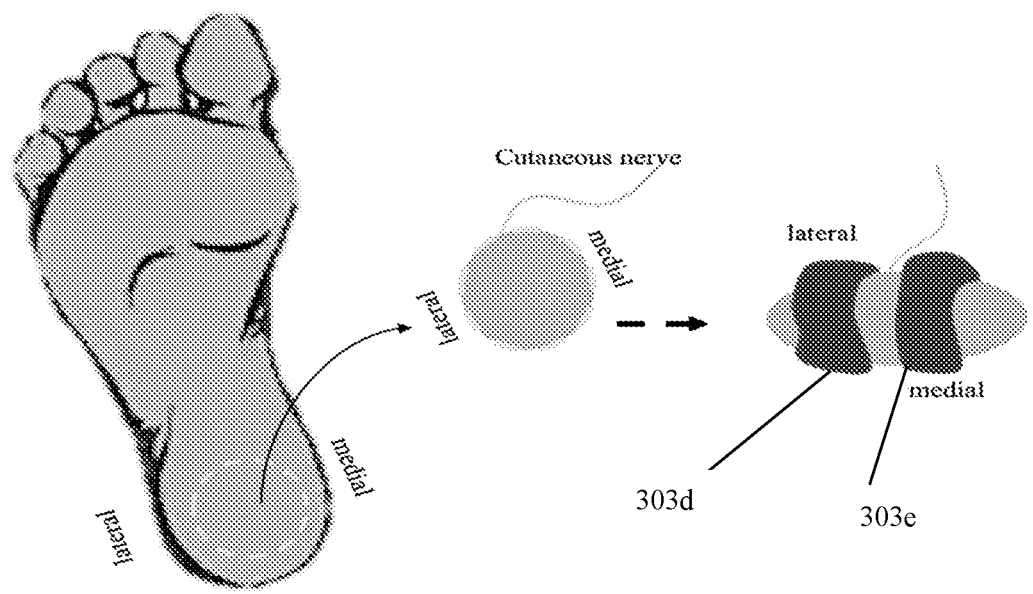
FIG. 17 is a schematic of a multi-cuff CMI.

An example of a cutaneous mechanoneural interface (CMI) is shown in FIGS. 5A and 5B. The CMI 30 includes a muscle actuator 301 and a skin flap 303. The skin flap is an end organ and includes a native or regenerative neurovascular structure 305. The muscle actuator 301 can be disposed in a partially or substantially circumferential configuration about the skin flap 303. As illustrated in FIGS. 5A and 5B, the muscle actuator 301 is disposed in a cuffed configuration with respect to the skin flap 303 and extends fully about the skin flap 303. Other configurations are possible. For example, the muscle actuator 301 can be disposed in a cuffed configuration with respect to the skin flap 303 and extend less than fully about the skin flap 303 (e.g., the muscle actuator 301 can be disposed from about 50% to about 95% around a circumference or perimeter of the skin flap 303, for example, 60%, 70%, 80%, 90% around the skin flap 303). Further configurations are shown in FIGS. 16A-16C. For example, a muscle actuator 301a can be disposed about a skin flap 303a such that the muscle actuator 301a is sutured to a surface of the skin flap 303a to induce contraction and extension of the skin (FIG. 16A). In another example, a pedicled skin flap 303b is sandwiched between a muscle actuator 301b and fascia 311 (FIG. 16B). Contraction of the muscle actuator of FIG. 16B can induce a constriction of the skin flap, producing sensations of static touch. In yet another example, a muscle actuator 303c is disposed in a conical configuration with respect to a skin flap 301c. Contraction of the muscle actuator 303c of FIG. 16C can cause constriction and sliding of the skin flap 301c out of the conical pocket. Any of the muscle configurations can be applied in multiple to a skin flap and in any combination. For example, as illustrated in FIG. 17, a skin flap can have two muscle actuators 303d, 303e disposed in a cuffed configuration.

The CMI can further include a device 307, such as an electrode, in operative arrangement with the muscle actuator 301 to stimulate muscle contraction. The device can be in communication with a controller 340 configured to provide a stimulation signal to the device 307 based on a signal received from a sensor of a wearable device (e.g., prosthetic hand 355 in FIG. 5A, or prosthetic device 455 in FIG. 10).

As illustrated in FIG. 5A, the wearable device is a prosthetic hand 355 that includes sensors 357, 359 disposed at, respectively, the fingertip areas and a palm area of the device. Communication between the electrode 307 of the CMI and the prosthetic hand 355 can be wireless. For example, as illustrated, the prosthetic hand 355 includes a wireless transmitter 353, and a controller 340 of the CMI can include or be in communication with a wireless receiver that receives sensory information from the transmitter 353.

The stimulation of the muscle actuator by the controller can include causing any of strain, constriction, compression, vibration, and sliding to be applied to the skin flap, either alone or simultaneously.

The native or regenerative neurovascular structure of the skin flip can include at least one mechanoreceptor, as illustrated in FIG. 5A. For example, the mechanoreceptor(s) can comprise any of Meissner corpuscles, Pacinian corpuscles, Ruffini corpuscles, Merkel cells, and free nerve endings.

Figure 10:
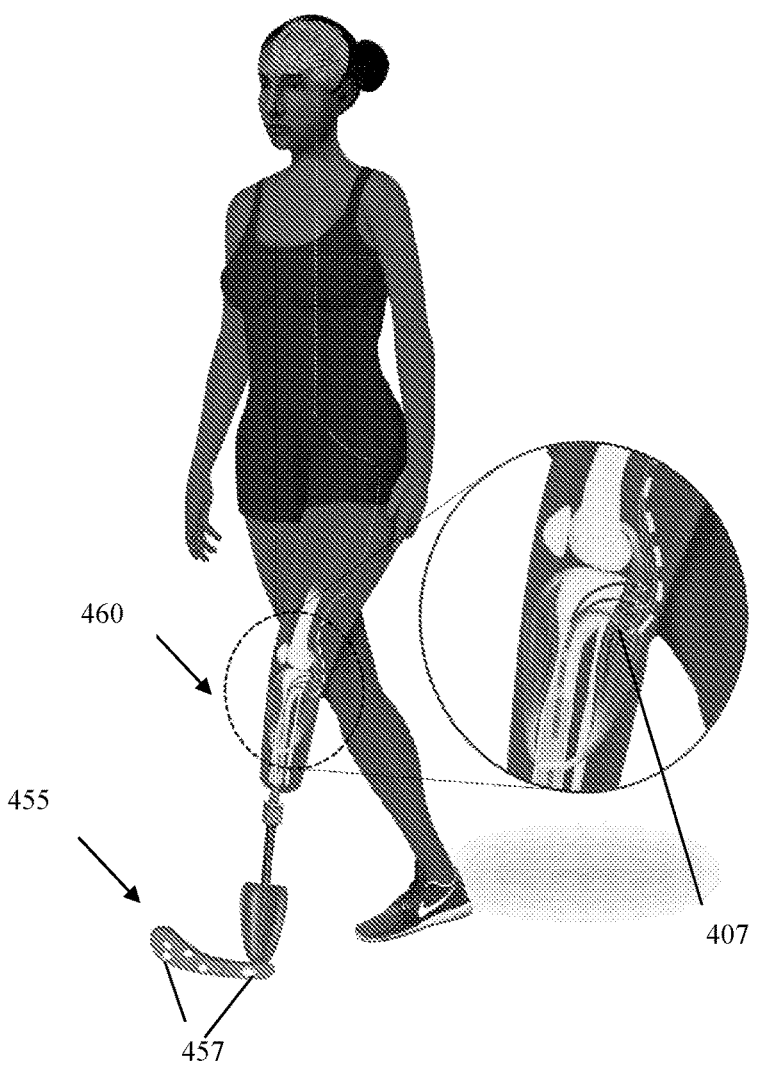
FIG. 10 is a schematic illustrating a CMI implementation in a subject with a lower extremity amputation and with an osseointegrated conduit.

As example of an osseointegrated CMI is shown in FIG. 10. As illustrated, the wearable device is a prosthetic foot 455 that includes sensors 457. The electrodes 407 in operative arrangement with a muscle actuator are tunneled through the osseointegrated implant 460.

Figure 6A:
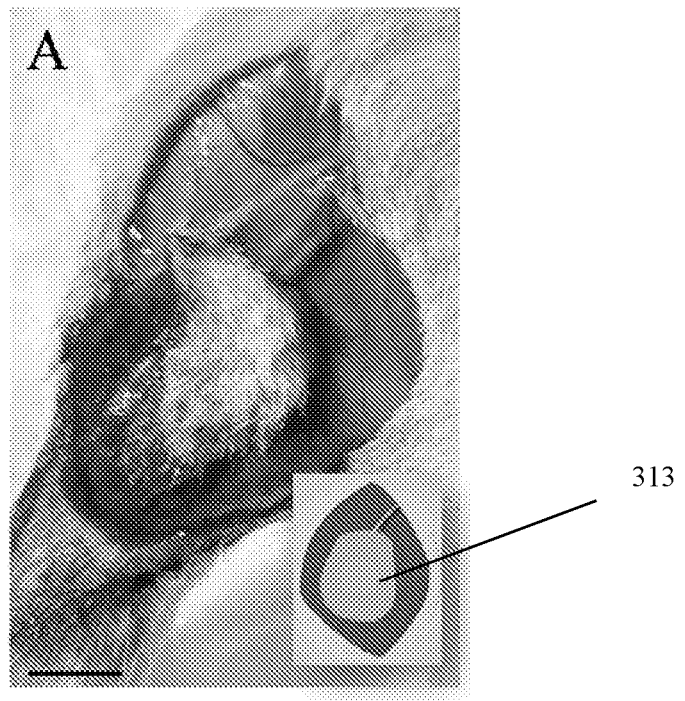
FIGS. 6A-6F illustrate construction and characterization of a CMI provided in a murine model.
Figure 6B:
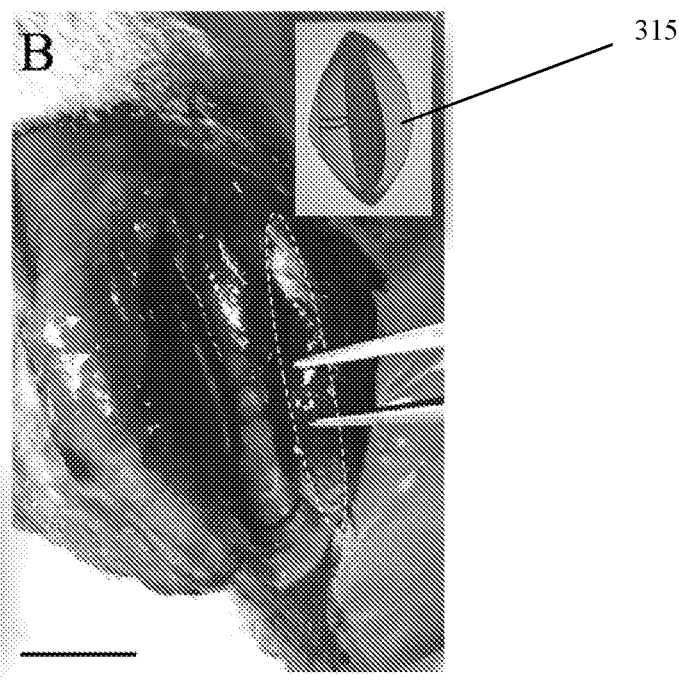
Figure 6C:
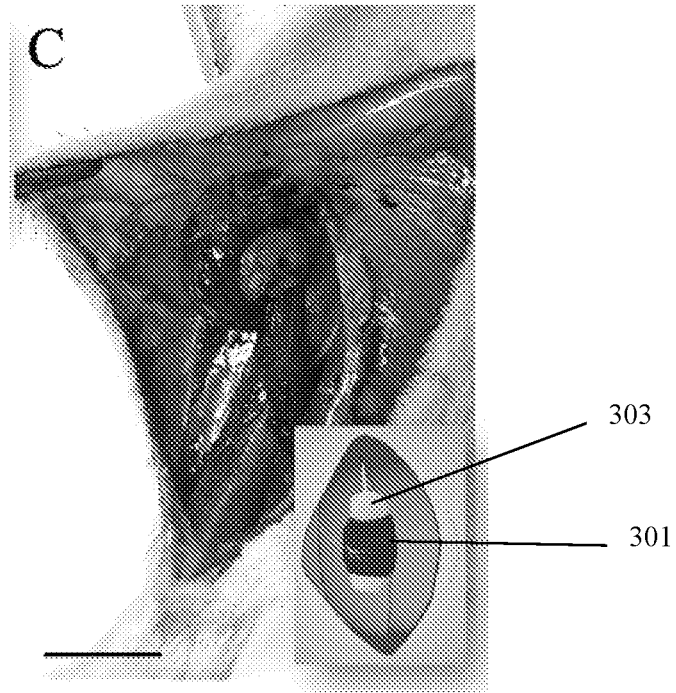
Figure 6D:
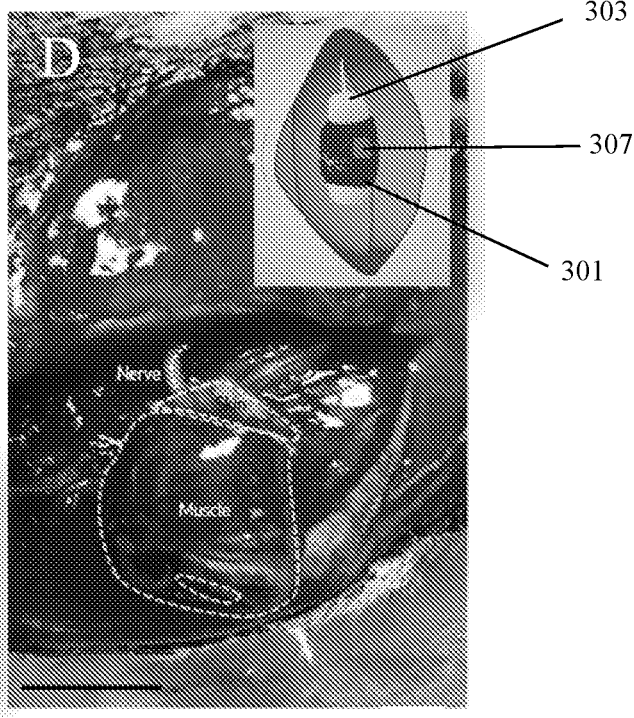

An example of a method of restoring at least partial sensory function of a limb is shown in FIGS. 6A-6D. The method includes surgically removing a patch of skin 313 from a body segment of the limb (FIG. 6A) and translocating the patch of skin to form a skin flap 303 at a non-anatomical portion of the individual (FIG. 6C). The method further includes disposing a muscle (e.g., muscle actuator 301) mechanically in combination with the skin flap. For example, a muscle 315 can be harvested (FIG. 6B), along with its vasculature, and wrapped about the skin flap 303 to form a muscle actuator 301 (FIG. 6C).

The skin flap includes at least one of a native or regenerative neurovascular structure. An output device (e.g., device 307) is disposed at or near the muscle (FIG. 6D) whereby electrical or optical signals can be transmitted by the output device to cause contractions of the muscle about the skin flap. The contractions can cause skin flap strain and a neural cutaneous afferent signal, thereby restoring at least partial sensory function of the limb.

Figure 28:
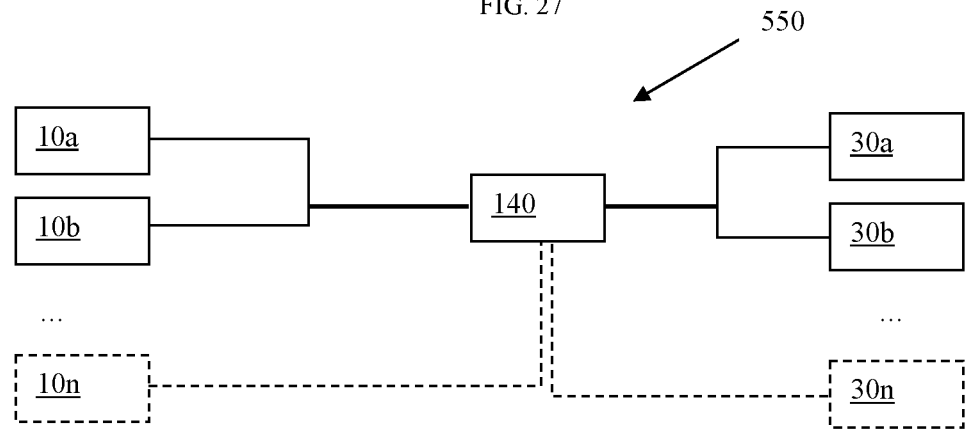
FIG. 28 is a diagram of an MI system.

The output device (e.g., device 307) can be connected to a sensory controller (e.g., controller 140, FIG. 28) associated with the prosthetic device, and sensory controller can be in communication with one or more sensors disposed at the prosthetic device for detecting application of at least one of pressure, shear, stress, strain, and vibration at the prosthetic device. The controller can be configured to stimulate the muscle (e.g., muscle actuator 301) via the output device based on sensor detection at the prosthetic device. For example, the controller can generate a graded touch sensation and/or a vibration at the skin flap.

Critical Role of Cutaneous Feedback

Cutaneous sensation plays a central role in our cognitive, emotional, developmental, and behavioral processes. As a multifunctional medium of exteroception, communication and protection, the skin utilizes specialized receptors (contact, pressure, shear, pain, vibration, and temperature) to create an intricate ensemble of distinct signals that are virtuously integrated by the peripheral nervous system. The resulting afferent feedback provides humans a sense of touch critical to tactile sensation, balance, motor and postural control, as well as grip and manipulation of objects.

The current amputation procedure discards the main cutaneous sensory end organs and provides no anatomical replacement for these substrates, despite their crucial role. Standard-of-care prosthetic systems focus primarily on restoring the mechanical components of an extremity with little to no neural control and no cutaneous feedback. Thus, patients experience a significant reduction in their sensory experience and motor function; for example, persons with upper-extremity amputation are often incapable of fine motor tasks such as buttoning a shirt. The decrease in functionality often results in a diminutive association of the prosthesis with their body, psychosocial distress and device abandonment. A growing body of evidence demonstrates the positive influence of neuroprosthetic sensory feedback in increasing confidence, mobility, functionality, and decreasing mental and physical fatigue. Thus, there is an unmet clinical need to design methodologies to restore sensation in a neuroprosthetic system following amputation.

Current Sensory Feedback Strategies

There are currently three prominent research approaches to relay cutaneous sensations from a prosthetic limb device: 1) peripheral nerve stimulation (PNS), 2) vibrotactile feedback and 3) mechanical actuation of residual skin following targeted sensory reinnervation (TSR).

In PNS, residual sensory nerves are electrically stimulated using an extraneural cuff electrode or an intraneural electrode array delivering various waveform patterns to evoke sensation. In preliminary studies, subjects undergoing PNS have demonstrated improved performance on object and texture discrimination, grip and gait tasks using sensation from bionic prostheses. However, in some cases, patients have reported tingling, parasthesias, an 'electrical' feeling or even shock-type sensations. The field has made great strides towards sensory encoding through the development of patterned waveforms and tactile stimulation models. However, the strategy for PNS involves interfacing directly with peripheral nerves, ideally requiring knowledge of the mechanotransduction and signaling patterns for each axon as well as the ability to selectively stimulate each axon. Finally, the manual, patient-specific, and time-consuming determination of stimulation site and parameters after implantation present an impediment to scalability.

Vibrotactile feedback is delivered using vibratory components (e.g., piezoelectric, voice coil or inertial transducer) mounted to non-native skin regions and activated by sensors in specialized prostheses. Patients learn to map the vibration sensed on their non-native skin sites to specific tactile prosthetic events. For many patients, such vibrotactile feedback cannot be properly decoded, can cause discomfort, and sometimes results in neural desensitization and skin irritation. The number of vibratory components is also constrained by the need for spacing between non-native stimulation sites that possess lower mechanotransducer densities. Thus, this approach has seen limited clinical implementation and acceptance among patients.

In TSR, cutaneous end organ nerves are surgically rerouted to non-anatomic skin sites. Following reinnervation, robotic actuators perform indentations on skin sites corresponding to forces, for example, measured at the fingertips of a robotic hand. However, this approach presents a number of fundamental and operational challenges. In TSR sensory end organs are created at the cost of eliminating native sensate areas. For example, chest sensation is given up in return for prosthetic hand sensation. Secondly, because reinnervation occurs alongside existing neural pathways, sensory specificity is lost and patients report a mix of native skin and prosthetic sensations at target stimulation areas. Finally, given power, weight, and attachment considerations, a scaled wearable electromechanical system, with external actuators functionalized for each anatomical skin region, proves practically challenging.

In summary, the existing approaches have had low specificity and a high barrier to implementation. Thus, a scalable sensory feedback modality capable of delivering more genuine, specific signals with a priori determination of sensory feedback sites is an important clinical goal.

Cutaneous Mechanoneural Interfaces

Biological tissues possess mechanisms that offer activation specificity, regenerative capacities, and high-energy efficiency. The Cutaneous Mechanoneural Interface (CMI) is a neural interface that can utilize the composite tissue architecture of a muscle-actuated skin flap, which can uniquely leverage the aforementioned properties, to restore cutaneous feedback (FIG. 5A). Out of the sensations perceivable by skin and measurable by prosthetic sensors, contact/pressure offers great value as it guides the majority of upper limb manipulations as well as lower limb reflexes, gait, and balance. A muscle can thus positioned in a cuff-like manner around a native or regenerative skin flap to enable graded sensations of contact. Upon functional electrical stimulation (FES), or any other form of artificial muscle stimulation, muscle activation applies a controlled strain or vibration on the skin proportional to an external sensation measured by prosthetic sensors. Mechanical deformation of the skin is transduced into afferent signals by free nerve (FN) endings and the four low-threshold mechanoreceptors (LTMRs) in skin, namely the Meissner corpuscles (MC), Pacinian corpuscles (PC), Ruffini corpuscles (RF), and Merkel cells (M) (FIG. 5A). Varied actuation modes can activate these slowly-adapting (SA) and rapidly-adapting (RA) receptors in different combinations to enable an array of sensations. Since the afferent signals will be generated by naturally-existent mechanoreceptors, which encode static touch, indentation, and vibration, and are transmitted through their natively innervated axons, the sensation is expected to closely approximate physiological sensation and map to homotopic sensory area.

The CMI merges advanced reconstructive surgery techniques with a sensorized prosthesis and an artificial muscle stimulation system to achieve a restoration of sensory cutaneous feedback for amputations of varying etiology and levels. In amputations resulting from chronic pain, limited trauma, joint instability, failed joint replacement, advanced arthritis, and most oncologic cases (estimated to be 20-45% of amputations), healthy distal tissues are available for use in a "spare-parts" surgical approach. In these cases, the CMI can be constructed utilizing a natively innervated skin flap. For example, in a patient with transradial amputation, skin flaps for each finger and the palm can be harvested with their intact neurovascular pedicles during amputation. In amputations resulting from complete trauma, vascular disease without comorbid diabetes, congenital limb deficiencies, and revision procedures where amputation has already occurred (estimated to be 50-70% of cases), there is minimal to no availability of distal tissues. In these cases, a regenerative approach can be taken, refunctionalizing the cutaneous nerve with a skin graft at a proximal junction where it is deemed to be viable. Intrafasciclar dissection of the cutaneous nerve can be performed to isolate individual branches. Branches can be grafted with a skin flap from a nearby donor site or discarded tissues. (See section herein titled Constructing CMI's through Regenerative Grafting for further technical details).

The CMI approach can scale up to the limits of intrafascicular dissection, providing anatomically distinct regions predetermined by fascicular anatomy. Muscle grafts (e.g., 4 cm×1 cm) can then be circumferentially cuffed around these skin flaps to create CMI's and positioned superficially on residual muscles. Electrodes can be sutured to each muscle graft and the leads to a wireless receiver/stimulator can be positioned in the residuum or tunneled through an osseointegrated implant (FIG. 10). During a patient's interaction with their environment, a specialized prosthesis can convey information from surface sensors (pressure, shear, vibration) to the implanted stimulator (FIG. 5A). Varied pulse sequences can cause activation of the muscle graft, constricting or vibrating the skin at varying magnitudes and frequencies to provide independent and anatomically-specific feedback signals for each region of the foot, for example (FIG. 10). The CMI presents a complementary approach to existing cutaneous feedback modes and uniquely leverages biological transducers without the need for external actuators.

The neuromechanical properties of CMIs were evaluated and are further described in Example 1 in the Exemplification section here.

Constructing CMI's Through Regenerative Grafting

For amputations in which minimal or no distal tissues are available, regenerative skin grafting can be performed to functionalize terminal cutaneous nerves with cutaneous end organs. Reinnervation of dermal flaps is commonly performed for various plastic surgery procedures using standardized neurorrhapy techniques, with successful sensory discrimination of the reinnervated flaps. The grafting of transected sensory nerves into a de-epithelialized skin graft have also been studied in the context of dermal sensory interfaces (DSIs) and shown to be reinnervated robustly with branching nerves of varying caliber and produced graded sensory nerve action potentials in response to stimulation.

Considerations for the Implementation of CMI's in Amputations of Vascular Etiology Approximately one-third of patients suffering from vascular disease results in occlusive effects, leading to critical limb ischemia, gangrene or other localized effects requiring amputation. In these cases, CMI's may be implemented using regenerative grafting in a more proximal setting. About two-thirds of vascular etiologies are comorbid with diabetes, manifest profoundly in the extremities, and are driven by systemic pathophysiology that preclude the adequate perfusion of vascular and nervous tissues. Among other processes in diabetes, microvascular disease, polypol pathway hyperactivity, oxidative stress, and inflammatory changes cause diffuse axonal loss and small fiber damage. Over half of individuals undergoing dysvascular amputations comorbid with diabetes will undergo a second amputation within 2 to 3 years and nearly half undergoing amputation for vascular disease will die within 5 years. Even within the population that remains relatively healthy, less than half are fitted or regularly use prosthetic devices due to a myriad of factors. In these subjects, concerns of revascularization and reinnervation potential, as well as the potential for prosthetic usage can contraindicate CMI's.

Proprioceptive Mechanoneural Interfaces (PMIs)

Recent work in proprioceptive neural interfaces involving dynamic muscle interactions is the Agonist-Antagonist Myoneural Interface (AMI). The AMI is a surgical and regenerative approach that seeks to restore both efferent motor control and afferent proprioceptive muscle-tendon feedback from both spindle fibers and Golgi tendon organs. The key advancement in this architecture is the surgical coaptation of agonist-antagonist muscle pairs within the residuum of an amputated limb. Preservation of the mechanical coupling between agonist contraction and antagonist stretch (or vice versa) allows activation of native mechanoreceptors within these mechanically linked muscles. In conjunction with a bionic limb, at least one AMI is surgically constructed in the amputated residuum for each prosthetic joint to be controlled, either by 1) rerouting agonist-antagonist musculature with native vascularization and innervation (native AMI), 2) connecting agonist-antago-nist neurovascular island muscle flaps (translocated native AMI), or 3) regenerating nerves that once innervated ago-nist-antagonist muscle pairs into deinnervated and nonvas-cularized muscle grafts (regenerative AMI). This diversity of surgical and regenerative approaches enables the AMI technique to be employed as either a native model or a regenerative model.

To achieve an agonist-antagonist muscle interaction, dis-crete agonist-antagonist muscle pairs are attached in series. In one attachment approach, shown in FIG. 1, the agonist 100 and antagonist 101 of a muscle pair 103, with their native Golgi tendon organs 104 and intrafusal muscle spindle stretch fibers 105, are sutured together tendon-to-tendon at one end 106 to form a series combination. The two free ends 107, 108 of the linearly-coupled, muscle-tendon arrangement are attached to a biological structure such as bone or fascia. The AMI's two muscles are both innervated by their respective motor nerves 109, 110. When the agonist 100 is electrically activated by the central nervous system (CNS) via motor nerve 109, its contraction causes the linked antagonist 101 to stretch, sending afferent information of muscle antagonist length, speed and force to the CNS via antagonist nerve 110. Similarly, when the antagonist 101 is electrically activated by the CNS via motor nerve 110, its contraction causes the linked agonist 100 to stretch, sending afferent information of muscle agonist length, speed and force to the CNS via agonist nerve 109. An agonist device, such as electrode 111, and an antagonist device, such as electrode 112, placed on each AMI muscle can be used to either sense electromyography (EMG) or electrically stimu-late each muscle to elicit contraction.

Further, each AMI muscle 100, 101 can also employ fascicle length and speed sensors 113, 114. For example, sonomicrometer crystals can be stitched into muscle fibers. Sonomicrometry is a technique of measuring the distance between piezoelectric crystals based on the speed of acoustic signals through the medium for which they are embedded, the medium for the AMI being muscle tissue. Typically, the crystals are coated with an epoxy and placed into the muscle facing one another. An electrical signal sent to either crystal will be transformed into sound, which passes through the muscle tissue, eventually reaching the other crystal, which converts the sound into an electric signal, detected by a receiver. From the time taken for sound to move between the crystals and the speed of sound through muscle, the distance between the crystals can be calculated, or the displacement of a muscle fiber. With a clock on the external micropro-cessor, the time rate of change of the crystal-to-crystal distance can be computed, or the muscle fiber velocity. Implanted elements 113 and 114 can also or alternatively comprise small magnetic beads coated in a biocompatible material. Using an array of magnetometers near the surface of the body adjacent the muscle (not shown in FIG. 20), the spatial location of each magnetic bead can be estimated, and hence the length/speed of each muscle. By sensing EMG, length and velocity, the force borne on each muscle can be estimated using a biophysical muscle model (e.g. Hill muscle model).

With these sensory data, a joint motor can be controlled in the external prosthesis in an open or closed-loop manner. In an open loop manner, for example, a motor controller can employ the position and speed of the agonist/antagonist muscle pairs to estimate desired prosthetic joint position and speed using a biomechanical limb model to map from the linear muscle space to the rotary prosthetic joint space, and servo to these desired values. To close the loop between the peripheral nervous system and the prosthesis, the motor controller can detect motion in the prosthetic joint, and map that rotary state information to the linear muscle space, relaying that information by artificially stimulating the antagonist to apply a closed-loop position control on the agonist (or vice versa). With agonist spindle feedback to the CNS, the individual wearing the prosthesis would then sense the change in position of the prosthesis. Further, a closed-loop force feedback from the prosthesis can be achieved; the motor controller can detect prosthetic joint torque, and map that rotary torque information to the linear muscle space, relaying that torque information into the nervous system by artificially stimulating the antagonist muscle to apply a closed-loop force control on the agonist (or vice versa). With agonist Golgi feedback to the CNS, the individual wearing the prosthesis can then sense the force, thereby causing the individual wearing the prosthesis to sense the torque applied on the prosthesis. Early results indicate that the AMI is capable of providing graded proprioceptive muscle-tendon feedback along native physiological afferent pathways, as well as improved efferent control of joint position and impedance. Further, the AMI has been shown to provide force feedback from an external prosthesis, enabling closed-loop neural force control from a robotic prostheses.

Although the AMI construct offers certain clinical advan-tages, there exist several limitations. First, to apply a con-trolled force onto the agonist, the agonists' muscle antago-nist is artificially stimulated. Similarly, to apply a controlled force onto the antagonist, that antagonists' muscle agonist is artificially stimulated. Since both muscles are innervated, such artificial activations cause afferent signaling of muscle length, speed and force of the artificially-stimulated muscle, causing the user to feel the muscle activation and dynamics of both muscles simultaneously. In distinction, within an intact biological limb, forces are applied to muscle from many different sources, such as gravitation and inertia. For example, during a walking gait, after the heel impacts the ground surface, the ankle joint typically plantar flexes, causing the tibialis anterior (TA) to stretch. Such a TA stretch is not caused by calf muscle activation and force generation; in fact, the calf muscle is typically not active during that phase of gait. To provide such a TA stretch using the AMI construct, the calf muscle linked to the TA would have to be artificially stimulated, but since the AMI calf muscle is innervated, the user would feel the calf muscle activation and dynamics, creating an artificial sensation to the amputee user.

Figure 20:
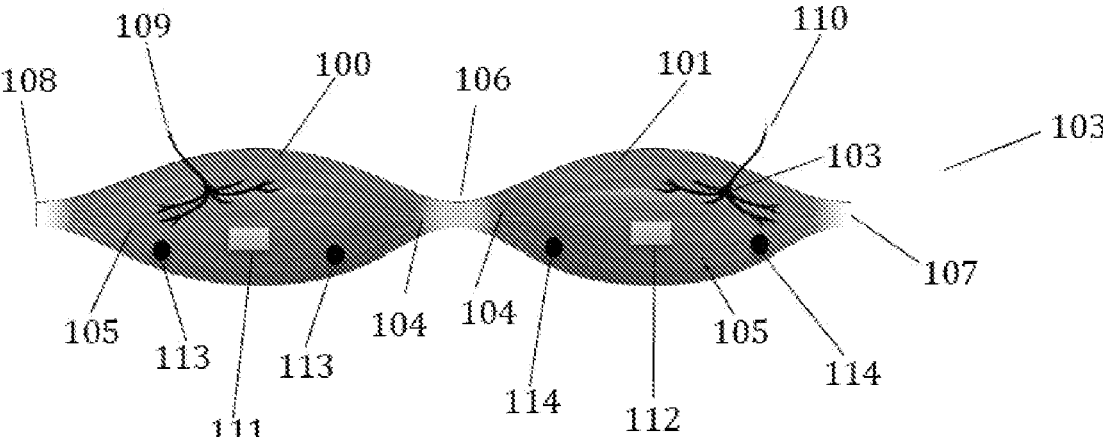
FIG. 20 is a schematic of an agonist-antagonist myoneural interface (AMI).

A second limitation of the AMI approach relates to the inability to emulate the biological transmission coupling all the muscles that span any particular biological joint. In an intact limb, when a muscle contracts, and that contraction moves a biological joint or joints, such movement causes other muscles that span the joint or joints to either be shortened or lengthened by varying degrees. Such a mechanical mapping from one muscle to the next is referred to herein as a joint or joints' biological transmission. The biological transmission is defined by each muscles' origin and insertion locations, the load on each muscle-tendon, and the moment arms across which each muscle acts. With the AMI approach, a muscle agonist is physically attached to a single antagonist using either a linear arrangement, such as shown in FIG. 20, or across a pulley that re-directs the line of muscle action using, for example, a synovial canal, an example of which is shown in U.S. Pat. No. 9,474,634, the entire contents of which are incorporated herein by reference. Once an AMI muscle pair is created, the transmission from the agonist to its single antagonist is fixed and is not likely to emulate the natural, intact limb transmission. Consequently, when the agonist contracts, it causes an unnatural level of stretch across its antagonist muscle, creating unnatural sensations for the amputee patient.

A third limitation of the AMI approach relates to difficulties associated with constructing a regenerative AMI. For a proximal limb amputation, either above-knee or above elbow, a two-stage surgical procedure is required to surgically construct regenerative AMI's. In a first surgery, a large proximal nerve undergoes a vesicular split wherein the large nerve trunk is split into finer fascicle bundles. At the transected end of each fascicle bundle, a muscle graft is placed. After several months, the nerve regenerates into the graft, and the graft also becomes fully vascularized. The muscle grafts cannot be linked into agonist/antagonist muscle pairs during the first surgery because the surgeon doesn't know a priori which fascicle bundle corresponds to the flexor, and which to the extensor of any particular joint. Hence, a second stage surgery has to be performed after each muscle graft has been innervated, and each fascicle bundle/muscle graft is electrophysiogically mapped to determine which bundle is the flexor and which is the extensor for each distal biological joint.

Figure 21:
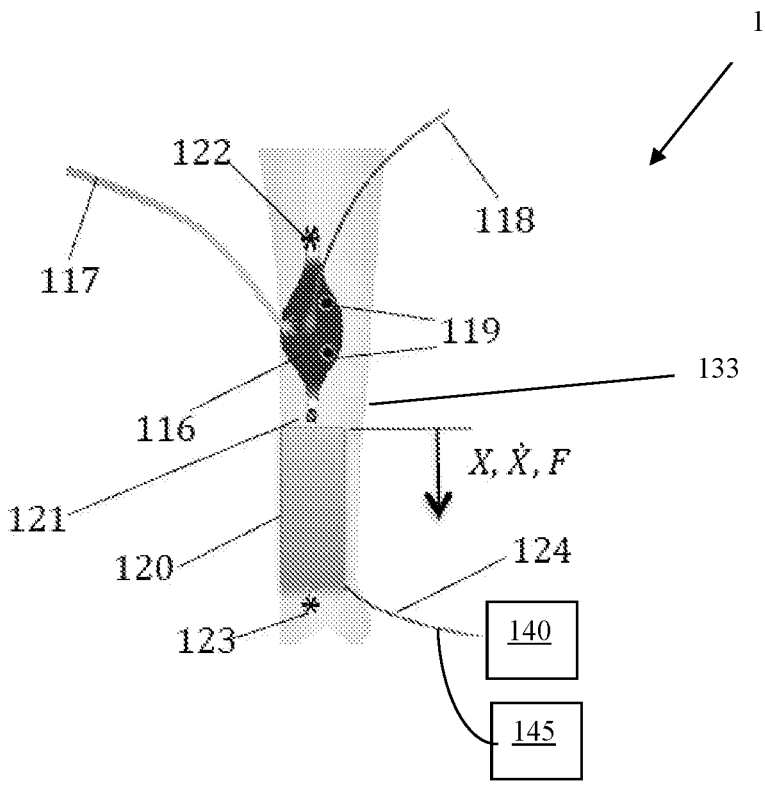
FIG. 21 is a schematic of a proprioceptive mechanoneural interface (PMI).

An example of a Proprioceptive Mechanoneural Interface (PMI) is shown in FIG. 21. PMIs can provide resolution to the difficulties noted above with respect to an AMI.

The PMI 10 includes an actuator 120 mechanically linked to a muscle end organ 116. The actuator 120 is configured to apply a force to the muscle end organ 116 and can be a synthetic actuator or a biological muscle actuator. The muscle end organ 116 includes an innervating nerve 117, which can be a native and/or regenerative neurovascular structure. The muscle end organ 116 can be one of an agonist-antagonist muscle pair and arranged with the actuator 120 such that actuation of the muscle end organ 116 can be provided independently of the other of the agonist-antagonist muscle pair. In particular, the actuator 120 can be in communication with a controller 140, which is configured to operate the actuator 120 based on a signal received from a prosthetic device (e.g., devices 355, 455). Communication between the controller 140 and the prosthetic device can be hardwired (e.g., as shown with respect to device 455 in FIG. 10) or wireless (e.g., as shown with respect to the device 355 in FIG. 5A).

As illustrated, the actuator 120 is implanted within a body segment 133 that also comprises the muscle end organ 116; however, the actuator may alternatively be disposed externally of the body segment 133. The actuator 120 is mechanically linked to the muscle end organ 116 through a link 121. For example, the muscle end organ 116 can be linked through a passive material connection, such as with a tendon, a ligament, fascia, a biological artificial material, or any combination thereof. The muscle end organ 116 can be mechanically linked to the actuator by cineplasty.

The muscle end organ can optionally include one or more devices 118, 119, such as sensors, that are configured to sense a state, change in state, or activation level of the muscle end organ. For example, the device 118 can be an electrode configured to sense an electromyography signal for controlling the prosthetic device. In another example, the device 119 is an implant configured to detect muscle fascicle length, speed, or combination thereof.

Figure 26:
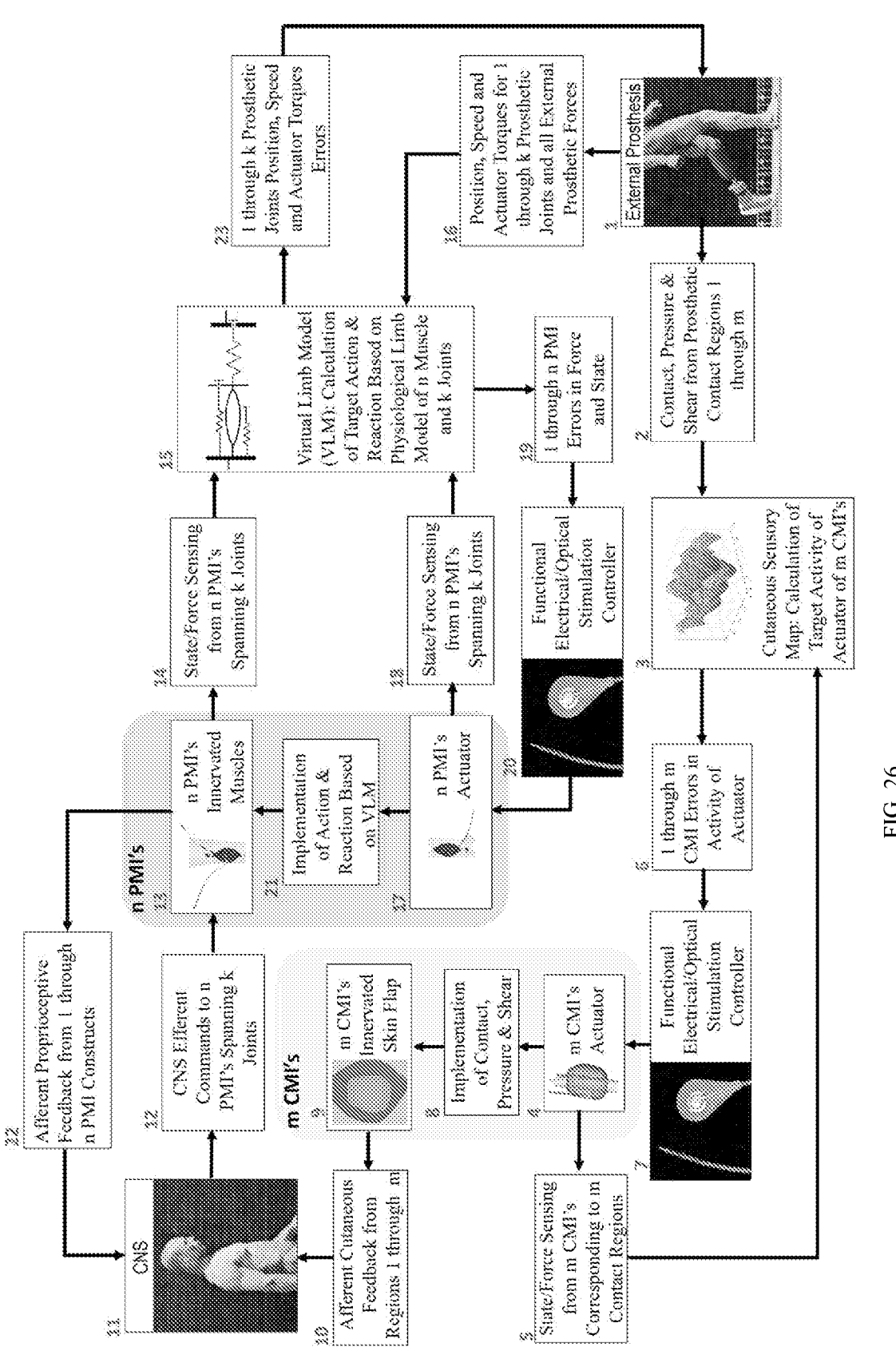
FIG. 26 is a control block diagram of mechanoneural interface controller (MIC) for a mechanoneural interface system.
Figure 27:
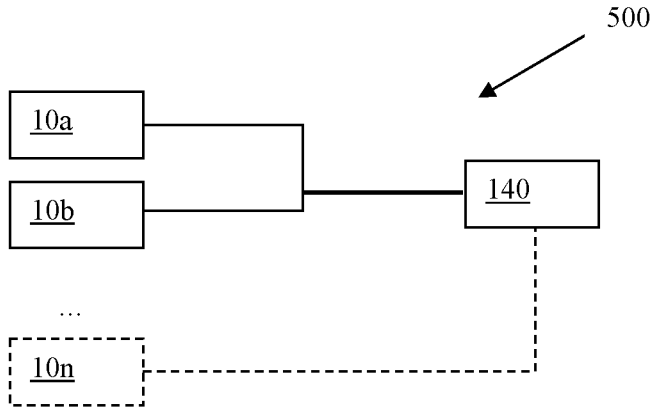
FIG. 27 is a diagram of a PMI system.

A proprioceptive mechanoneural interface system 500 (FIG. 27) can include at least two PMIs (10a, 10b, . . . 10n), each PMI being independently actuatable by a controller 140. A mechanoneural interface system 550 (FIG. 28) can include at least two PMIs (10a, 10b, . . . 10n) and at least two CMIs (30a, 30b, . . . 30n) actuatable by a controller 140. The systems 500, 550 can be operated by a control system (e.g., a Mechanoneural Interface Controller (MIC) as shown in FIG. 26 and further described below) to provide afferent proprioceptive and/or cutaneous feedback to an individual wearing a prosthetic device and, optionally, efferent signals for control of the prosthetic device.

Using regenerative, surgical and biomechatronic techniques, for each muscle that is to be represented in a prosthetic control system, one PMI can be constructed within the affected limb. As illustrated in FIG. 21, a vascularized muscle end organ 116 is shown with innervating nerve 117. Muscle end organ 116 can comprise artificial sensors, such as an electrode 118 attached to the muscle 116 and configured to measure electromyography (EMG) due to efferent stimulations via nerve 117. Muscle end organ 116 can comprise implants 119 configured to measure muscle fascicle length and speed. For example, implants 119 can be small magnetic beads (e.g., 1 mm to 3 mm diameter) with a thin biocompatible coating, such as titanium or Parylene. An array of magnetometers positioned adjacent muscle 116 (not shown in FIG. 21) on or near the skin surface are used to measure the magnetic fields created by magnetic beads 119. From these field measurements, a magnet tracking algorithm can compute the location of each magnet, the distance between each magnet, or both.

Additional descriptions of systems and methods relating to tracking of magnetic objects can be found in WO2019/074950, "Method for Neuromechanical and Neuroelectromagnetic Mitigation of Limb Pathology;" the teachings of which are incorporated herein in their entirety. Additional descriptions of systems and methods relating to tracking of multiple targets, such as permanent magnets, can be found in the following publication: Cameron R Taylor, Haley G Abramson, and Hugh M Herr. Low-latency tracking of multiple permanent magnets. IEEE Sensors Journal, 19(23): 11458-11468, 2019; the teachings of which are incorporated herein in their entirety.

Alternatively, or in addition, implants 119 can be sono-micrometry crystals used for the measurement of muscle length and speed. Using a biophysical muscle model (e.g., the Hill Model), the force borne by muscle 116 can be estimated with inputs of EMG from electrode 117, as well as muscle length and speed from implants 119.

The PMI also comprises an actuator 120 mechanically attached in series with muscle end organ 116 via connecting link 121. Muscle end organ 116 is attached at its opposite end at 122 to a biological material such as bone, fascia, or other anchoring material known in the art. Control and/or power signals can be transmitted through a wired or wireless connection 124 from a controller 140 and/or power supply 145, respectively, which can be located on the external prosthesis. Through microcontroller signaling, the length (X), speed (Ẋ), and force (F) of the muscle end organ 116 can be controlled via actuator 120 to modulate the afferent mechanoneural proprioceptive transduction into the CNS of the individual. It would be understood by those of ordinary skill in the art that actuator 120 can be implemented in a number of distinct ways, for example, with use of a biological muscle, an implantable synthetic actuator, or an external synthetic actuator.

The PMI can includes a biological muscle actuator 120 mechanically attached in series with the muscle end organ 116, and the link 121 can be provided by a passive material connection, such as biological tendon, ligament, or fascia. Alternatively, muscle end organ 116 can be connected to muscle actuator 120 with a passive biocompatible material, such as AlloDerm™ (Allergan). Similarly, the muscle actuator 120 is attached at its opposite end at 123 to an anchoring material, such as bone, fascia or other materials known in the art. Alternatively, muscle end organ 116 can be attached to muscle actuator 120 end-to-end, where tendon 122 is directly attached to tendon 123 creating a loop or ring wrapping around a limb, for example. Further, the connection 124 of the muscle actuator can include or provide for an output device, such as a stimulating electrode or light-emitting diode, for the application of microprocessor-controlled stimulations for the application of controlled forces (F) or displacements (X, Ẋ) onto muscle end organ 116 that are correlated to measured forces or displacements from an external prosthesis. In so doing, such control actions can modulate the afferent mechanoneural proprioceptive transduction into the CNS, providing the wearable robotic user natural proprioceptive sensations.

The PMI can alternatively, or in addition, include an implanted synthetic actuator 120 mechanically attached in series with muscle end organ 116 using a passive material connection 121, such as biological tendon, ligament, fascia, or a biocompatible artificial material such as AlloDerm™ (Allergan). Such an implantable actuator can be biocompatible and made from, for example, an electrically-active polymer, a pneumatic artificial muscle, or a hydraulic artificial muscle. Similarly, on its opposite end, actuator 120 is mechanically grounded at point 123 onto an anchoring material, such as biological tendon, ligament, fascia, or a biocompatible artificial material, such as AlloDerm™ (Allergan).

For example, the actuator 120 can be a linear hydraulic actuator with hydraulic power lines running through the center of an osseointegrated implant, such as the implant shown in FIG. 10. In such an arrangement, a hydraulic power supply can be external to the body, with hydraulic tubes passing from the external prosthesis through the osseointegrated implant and into the body to power hydraulic actuators 120 for each PMI construct.

Figure 22:
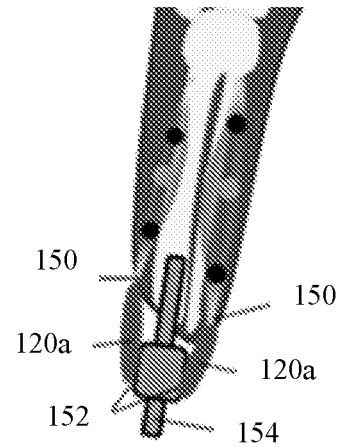
FIG. 22 is a schematic of an osseointegrated platform for mechanoneural interfaces.

In another example, the PMI can include an external synthetic actuator 120 mechanically attached in series with muscle end organ 116 via cineplasty where the synthetic actuator 120 is located external to the body. Surgical procedures such as muscle tunnel cineplasty, or tendon exteriorization cineplasty, can be employed to externalize the force and excursion of muscle end organ 116 and tendon 121 onto external synthetic actuator 120. Through this approach, the synthetic actuator 120 is external to the body, and thus can apply force and displacements to muscle end organ 116 without the requirement of biocompatibility. Osseointegrated implants have been successfully implanted in lower and upper-extremity amputees, providing stable mechanical attachment of prosthetic componentry to the residual bone. In FIG. 22, external synthetic actuators 120a attach to muscle end organs via cineplasty at locations 150, and are mechanically grounded at location 152 onto an external device such as an osseointegrated implant 154.

An advantage of the PMI is that it comprises an actuator 120 that can apply controlled forces and displacements onto the innervated muscle end organ 116 without the human prosthetic user experiencing unnatural proprioceptive sensations caused by the actuation itself. In particular, the actuator 120 is without a native innervating nerve, and, thus, it can be activated via microprocessor-controlled artificial signaling without an afferent signal being sent to the CNS causing unnatural proprioceptive sensations. For example, if actuator 120 were a muscle, the muscle can be denervated and an output device, such as a stimulating electrode, can be used to apply either electrical or optical stimulations to elicit muscle contractions for the purpose of controlling the forces and displacements applied to end organ 116, as well as to maintain the mass and contractility of muscle actuator 120. Alternatively, muscle actuator 120 can be innervated using a cutaneous nerve taken from a denervated patch of skin; in this approach, artificial stimulations of muscle actuator 120 would then not induce proprioceptive signaling to the CNS that might confuse the amputee user. In turn, the cutaneous nerve innervating the muscle actuator 120, in combination with artificial muscle stimulations, can serve to maintain contractility and morphology of the muscle.

Another advantage of the PMI is that the actuator 120 can apply forces onto agonist muscle end organ 116 independent of antagonistic muscle activation, or vice versa. For example, consider the example of heel strike in a walking gait cycle when the tibialis anterior (TA) is actively stretched within an intact limb during controlled plantar flexion. To emulate this phase of gait for a person with transtibial amputation, the active PMI within the amputated leg residuum can comprise the TA as the muscle end organ 116 and an actuator 120 attached in series with the TA. Using a neuromechanical model of the intact limb (e.g., OpenSim), referred to herein as a Virtual Limb Model (VLM), the length, speed, and force that would be experienced by the TA if, in fact, the TA were physically coupled across the prosthetic ankle can be estimated. Such an estimate can be achieved using the biophysical VLM with prosthetic sensory inputs, such as prosthetic ankle position, speed, and torque, as well as ground reaction force and center-of-pressure.

These biomimetic muscle dynamic parameters of length, speed and force can then be employed as control targets for the actuator 120. Here, the PMI Virtual Limb Controller (VLC) would servo the TA muscle end organ 116 of the PMI to the desired biomimetic length, speed, and force targets via actuator 120 and artificial signaling via wired or wireless communications 124. In this feedback controller, errors in muscle end organ length, speed and force can be computed in each control cycle by subtracting the desired length, speed, and force estimated from the biomimetic VLM from the actual length, speed, and force measured directly from the PMI, such as with sensors 118 and 119. The VLC can then servo the actuator 120 to mitigate these errors, and, in so doing, control the mechanoneural proprioceptive transduction into the CNS. Furthermore, if the stroke length and muscular force capacity of muscle 116 is affected due to an amputation or regenerative model, the readings from the PMI sensors 118 and 119 can be scaled prior to input to the VLM. Similarly, the position, velocity, and joint torque of the prosthetic joint can also be scaled appropriately to match the physiological capacity of the muscle end organ 116 after amputation.

At least two PMI's may be provided to control a single rotary prosthetic joint. For example, for flexion-extension free space movements of a 1 degree-of-freedom prosthetic joint, as shown in FIGS. 23A and 23B, one PMI 10*a* comprises a joint flexor muscle 126, and a second PMI 10*b* comprises a joint extensor muscle 134. These two PMI's can form a PMI system and be used for the efferent-afferent neural control of a computer-controlled prosthetic joint within a leg or arm prosthesis. When the CNS sends an efferent signal to activate muscle end organ 126 via nerve 127, the muscle contracts. EMG sensor 128 and state sensors 129 measure muscle EMG and muscle state, respectively. These proprioceptive data are then sent to a microprocessor on the external prosthesis. Using a biophysical model (e.g., Hill Muscle Model), the force borne by muscle end organ 126 is estimated, and then the prosthetic micro-computer uses these sensory proprioceptive data to control a synthetic motor to actuate the prosthetic joint in a flexion direction. In this example, the prosthetic joint position can be controlled using a computed error between the external joint's actual measured position, as measured using a prosthetic sensor, such as a joint encoder, and a desired joint position. Such a desired rotary position can be estimated using a VLM to map from the linear muscle-tendon space for the muscle 126 to the rotary prosthetic joint space. Here, the total muscle-tendon length of flexion end organ 126 can be estimated from: 1) a measured fascicle length from state sensors 129, and 2) a total tendon length estimated using the muscle organ's tendon stiffness and the force borne onto that muscle's end organ. With this total muscle-tendon length, the target joint position can be estimated using the biophysical origin and insertion points of the representative muscle, and the joint moment arm across which the representative muscle acts. The VLC can then servo the prosthetic motor to mitigate the position error between this target position and the measured joint position.

For afferent feedback, as flexion end organ 126 contracts, its corresponding in-series actuator 130 applies a force onto end organ 126 through output device 131 artificial muscle stimulations to simulate the forces necessary to overcome gravity and inertia as the prosthetic ankle-foot complex accelerates into dorsiflexion. These gravitational and inertial forces are estimated using the VLM using the measured prosthetic ankle-foot positions and accelerations. In addition, as flexion end organ 126 contracts, actuator 132 also contracts via artificial muscle stimulations from output device 133, stretching the extensor muscle end organ 134 to create the proprioceptive sensation of an agonist-antagonist muscle interaction. In this example, the actuator 132 applies a closed-loop position control onto the extensor end organ 134 with feedback signals of end organ length, speed and force via EMG sensor 135 and state sensors 136. The VLM can be used to estimate the change of position and speed that the actuator 132 applies onto the extensor end organ 134 during each control cycle to simulate the biological trans-mission between agonist contraction and antagonist extension.

For an ankle plantar flexion movement, an efferent command is sent to extensor end organ 134 causing a contraction via nerve 137. To create afferent feedback, as extension end organ 134 contracts, its corresponding in-series actuator 132 applies a force onto end organ 134 through output device 133 artificial muscle stimulations to simulate gravity and inertial forces as the prosthetic ankle-foot complex accelerates into plantar flexion. These gravitational and inertial forces can be estimated using the VLM using the measured prosthetic ankle-foot positions and accelerations. In addition, as extensor end organ 134 contracts, actuator 130 also contracts via artificial muscle stimulations from output device 131, stretching the flexor muscle end organ 126 to create the proprioceptive sensation of an agonist-antagonist muscle interaction. Here, actuator 130 applies a closed-loop position control onto the flexor end organ 126 with feedback signals of end organ length, speed and force via EMG sensor 128 and state sensors 129. The VLM can be used to estimate the change of position and speed that actuator 130 applies onto flexor end organ 126 during each control cycle to simulate the biological transmission between antagonist (extensor) contraction and agonist (flexor) extension.

An efferent torque control can also be implemented. Here, the prosthetic joint torque can be controlled using the computed error between the actual torque output of the prosthetic joint actuator, as measured using a torque sensor, and a desired biophysical joint torque. Such a desired torque can be estimated using a VLM to map from the linear muscle-tendon force for each muscle 126 and 134 to the rotary prosthetic joint torque. Here the torque contribution of each muscle-tendon 126 and 134 is summed to estimate the desired biophysical joint torque. The VLC then servos the prosthetic actuator to mitigate this torque error. In the next section, surgical techniques are presented for PMI construction.

Surgical and Regenerative Tissue Techniques to Create PMI's.

Native PMI: Surgical Strategy Incorporating Native Muscles.

In primary elective amputations or those in which sufficient residual neuromusculature exists, each native muscle can be utilized to create components of the PMI, namely end organ muscle B and muscle actuator D (FIG. 24). Each native muscle can remain in its native configuration at its origin. Then, one of the following strategies can be utilized for the creation of the muscle actuator D.

Strategy one: Each native muscle is transected into approximately two equal components, while maintaining the vascular leash to each segment or as a free flap for the muscle actuator segment D. Such a transection can be relatively perpendicular to the longitudinal axis of the native muscle, or relatively parallel to its longitudinal axis.

By segregating the original native muscle into approximately two equal components, one can assure that the force-tension and force-velocity behaviors of each component are comparable. Clearly, if actuator D were too small, full proprioceptive feedback could not be achieved; if the muscle actuator D were substantially smaller in physiological cross-sectional area as well as length, such an actuator may be incapable of applying the necessary forces and displacements onto end organ B to broadly impose the full range of proprioceptive signaling to the CNS. More specifically, the volume of actuator D can be slightly larger than that of end organ B in the case where actuator D is denervated. In this case, actuator D may experience denervation atrophy even with regular electrical stimulation to preserve muscle mass. Thus, a greater starting volume of muscle in D can enable an equilibrium point at which B and D are equally sized.

With a largely perpendicular transection, the distal segment can then be utilized for the muscle actuator D. For example, the distal segment, or actuator D, can be flipped such that the tendon (which normally inserts into the distal joint) is utilized for linkage C. In this case, muscle end organ B is debulked and shortened to create a narrow linkage segment for D. If the physiological cross-sectional area of end organ B is comparable to that of the tendon of actuator D, a direct muscle-tendon coaptation can be performed using suture. If the diameters do not match, then a tendon graft may be placed onto end organ B and then coapted with actuator D using standard suturing methodologies. A tendon graft, goretex patch, or silicone sleeve may be utilized to further stabilize the muscle-actuator linkage C. Alternatively, instead of flipping the distal segment after transection, a passive material of either biological origin, such as tendon or ligament, or synthetic origin, such as AlloDerm, can be used for the passive connection C between the proximal and distal halves of the original native muscle, forming end organ B and muscle actuator D, respectively.

Figure 25:
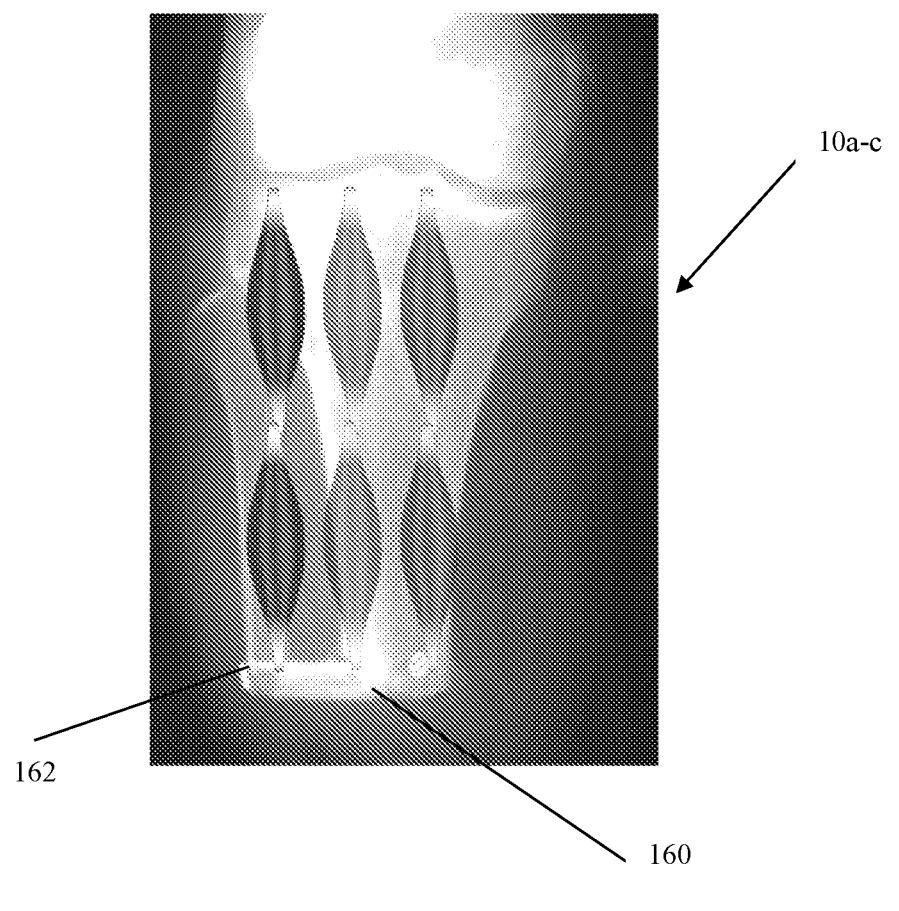
FIG. 25 is a diagram of a multiple PMI arrangement.

Fixation of the actuator at E may be performed by suturing the distal segment of actuator D to the fascia bed, a ligamentous structure, a tendon, or a bone. To provide a robust mechanical linkage, tendon grafts or artificial tendon grafts may be utilized to gather the muscle fibers and provide a robust substrate for suturing. A bone bridge 160, such as that created during an Ertl amputation may be created to provide a bony structural landing pad for the actuating muscles of each PMI 10a-c (as pictured in FIG. 25). In this case, bone anchors 162 may be utilized to create a secure fixed end for the actuator at E. Osteo-tendinous grafts, similar to those that are used for ACL repair, can be prepared to enable a more robust attachment of actuator D to bone. Synthetic polymer composites may also be used to form tendon-cartilage attachments and may be inserted or sprayed onto E. Overall, this strategy will provide relatively linear positioning of muscles B and D.

In distinction to a relatively perpendicular muscle transection to form a native PMI, a longitudinal transection can be performed to divide the original native muscle into approximately equal halves. For a largely longitudinal transection, one muscle segment of the original native muscle can be utilized for end organ B, while the remaining adjacent segment can be utilized for actuator D. In this approach, the muscle segments share the same proximal origin tendon at A, and then pass origin-to-insertion in adjacent somewhat parallel orientations. At the distal end each muscle segment B and D can each have its own tendon segment that can pass through a tarsal tunnel/synovial canal or a tendon graft fabricated in a tunnel-like architecture. Such a tunnel or canal can be attached to underlying fascia or bone, and can serve as a pivot such that when end organ B contracts, muscle actuator D is stretched (and vice versa) in an agonist-antagonist relationship. Bone anchors may be utilized to secure the tunnel structure to bone, if anchored on bone. Acellular matrices, such as decellularized skin, tendon, or fascia, may be utilized to create the tunnel as well. Fascia and acellular matrices may also be utilized to cover C and prevent excessive scarring that would preclude the facile excursion/actuation of muscles B and D. Alternatively, the sliding tunnel can be constructed with a biocompatible synthetic material such as AlloDerm. The tunnel can be located on the same side of the bone as the shared muscle origin, or on an adjacent or opposite side, requiring the end organ B and actuator D to be wrapped around the bone before their respective tendons pass through the tunnel or canal.

For either the transverse of longitudinal transections, if actuator D is not able to maintain a native vascular leash, it can be prefabricated. Blood vessels in the nearby regions can be grafted to D to enable rapid angiogenesis and maintenance of vascular supply.

In an example, actuator D is denervated through the blunt dissection of any nerve branches segmentally innervating that muscle segment. Consequently, when muscle actuator D is artificially stimulated by a prosthetic control system, the amputee user does not experience unnatural proprioceptive sensations. Alternatively, muscle actuator segment D can be innervated using a cutaneous nerve taken from a skin patch that has been denervated; in this approach, artificial stimulations of muscle actuator D does not induce proprioceptive signaling to the CNS that might confuse the amputee user. In turn, the cutaneous nerve innervating muscle actuator D, in combination with artificial muscle stimulations, can serve to maintain its contractility and morphology.

Strategy two: Supplemental native muscles on the opposing side of the end organ native muscle may comprise actuator D. For example, a muscle in the posterior compartment may serve as actuator D for an end organ muscle in the anterior compartment. The size of end organ B and actuator D can be closely matched for optimal operation. Muscles selected for actuator D may be synergists or muscles for which no prosthetic counterpart exists. These muscles can be left inserted at the origin E and denervated through blunt transection of their primary nerve and left denervated, or alternatively, reinnervated using a cutaneous nerve. A regenerative peripheral nerve interface (RPNI) can be created at the end of the motor nerve for neuroma prophylaxis. Then the distal tendons of actuator D and muscle end organ B can be linked through tendon-to-tendon coaptation. This point of coaptation C can be positioned strategically to prevent subluxation. Linkage C may be coupled to the underlying fascia or bone through the use of a tarsal tunnel/synovial canal or a tendon graft fabricated in a tunnel-like architecture to allow sliding and agonist-antagonist muscle interactions between the end organ B and actuator D. Bone anchors may be utilized to secure the tunnel structures to bone, if anchored on bone. Acellular matrices, such as decellularized skin, tendon, or fascia, may be utilized to create the canals as well. Fascia and acellular matrices may also be utilized to cover C and prevent excessive scarring that would preclude the facile excursion/actuation of muscles B and D. Attachment E for the supplemental muscle can be its origin point at the bone. Overall, this strategy can provide U-shaped architectures for the PMI with the connection point C between the muscles passing through the sliding pivot formed by the tarsal tunnel, synovial canal or tendon graft.

Strategy three: Synthetic polymer-based actuators, piezoelectric actuators, or hydraulic actuators may be utilized for actuator D. Depending on the structure of the proximal and distal ends of D, C and E may be created utilizing coaptations, tendon-grafts, acellular matrix sheets and could be situated on bony or myofascial platforms.

Regenerative PMI: Surgical Strategy Incorporating Regenerative Muscles.

Free flap muscle grafts for end organ B and muscle actuator D can be harvested from any location in the body. These grafts may be up to 4 cm×2 cm and up to 2 cm in height. Grafts with a tendinous component are preferable. These muscle grafts can be surgically coapted at their ends, with tendon grafts or acellular matrices positioned in between the grafts to provide electrical isolation at C. The regenerative PMI can then be situated on a relatively flat section of clean fascia to excurse with ease and minimize undesired scarring, respectively. Then connections A and E can be created by suturing B and D to the underlying muscle fascia. If a bone surface is available, connections A or E may be affixed to the bone utilizing bone anchors or suturing to the cartilage. A sheet of adhesion barricade or acellular matrix may be placed underneath the PMI, especially when the fascial plane is not clean or comprised of a planar fascia. This sheet can enable greater electrical isolation and mechanical sliding through the prevention of adhesion or scarring to underlying constructs.

Motor nerves in the limb can undergo intrafascicular dissection to yield as many discrete fascicular units as possible. Each of these units can be placed in a PMI's end organ muscle B and reinnervate the regenerative graft. A small muscle pocket will be created towards the middle of the muscle end organ B. The nerve can be freshly transected or re-transected to create a clean distal surface. Epineurial sutures will be used to secure the nerve to the inner surface of the muscle pocket. Additional epimysial sutures can be used to close the muscle pocket. Additional epineural sutures can be used to secure the nerve leash to surrounding tissue, if demanded by the local architecture. Following reinnervation, electrical stimulation or muscle sensing can be utilized to identify each PMI to determine its functional identity (e.g., flexor/extensor and which flexor/extensor).

For all strategies incorporating biological muscle, the volume of actuator D can be slightly larger than that of end organ B in the case where actuator D is denervated. In this case, actuator D may experience denervation atrophy even with regular electrical stimulation to preserve muscle mass. Thus, a greater starting volume of muscle in D can enable an equilibrium point at which B and D are equally sized. Magnets may also be placed in C if sufficient bulk is available in this structure. Hardware may also be placed in underlying tissues to serve as a 'static' reference point for the relative movements of B and D.

Hardware Implantation.

For all strategies and configurations, stimulating electrodes may be implanted on B and D. Intramuscular, epimysial or fine wire electrodes may be placed. Sonomicrometry crystals or magnets may be introduced into the bulk of the muscle and can be targeted towards the center of the bulk. For each, a muscle pocket can be created using a sharp and narrow blade. Then, an introducer tool can be used to position the hardware deep inside the muscle. Layered sutures can be utilized to secure the hardware and close the muscular pocket. Any leads for hardware can be situated in parallel to the muscle fibers to enable sliding in a direction that is complementary to the movement of the constructs. A stress-strain loop can be created in leads before they are tunneled to their superficial or osseointegrated port to prevent undesired stretching or tugging during gross movement of the limb.

General Description of the Mechanoneural Interface Controller (MIC) Comprising m CMI's, n PMI's and a k Degree of Freedom (DoF) External Prosthesis.

A control system for m CMI's, n PMI's, and a k DoF prosthesis is provided. The Mechanoneural Interface Controller (MIC) is shown in FIG. 26. The m CMI's can be implemented in which each CMI construct corresponds to a distinct contact region of the external prosthesis for a total of m prosthetic contact regions. By applying appropriate mechanical stimulation to each innervated skin flap through each CMI's actuator, the physiological afferent cutaneous feedback of m contact regions can be provided. Similar to the single PMI pair case, the n PMI's can be constructed for a k DoF external prosthesis based on physiological dynamics. The PMI's corresponding to monoarticular muscles (e.g., single joint flexor/extensors) for k DoF can be added, as well as the PMI's of bi-articular muscles such as the gastrocnemius and rectus femoris. Theses n PMI's can virtually interact through a virtual limb model (VLM). The generalized Mechanoneural Interface Controller (MIC) is described below.

The MIC can provide for bi-directional control with afferent proprioceptive and cutaneous feedback by PMI's and CMI's, respectively, to achieve kinesthetic sensations across multiple joints of an external prosthesis. An example of a MIC control scheme is shown in FIG. 26.

In short, the MIC is configured to operate the CMIs and PMIs of a system based on signal(s) received from sensor(s) of a prosthetic device, and each PMI and each CMI can be independently actuated to prevent unnatural sensations in the wearer of the prosthetic device. Further, each PMI can include at least one device disposed at the muscle end organ that is configured to sense a state, change in state, or activation level of the muscle end organ, such that the controller can provide efferent control of the prosthetic device. The controller can be configured to determine a target action and reaction of the prosthetic device based on a virtual limb model (VLM). The controller can further be configured to determine an error in target action and reaction of the prosthetic device based on the virtual limb model and provide for adjusted actuation of the PMIs.

Further, each CMI can include at least one device configured to sense a state or change in state of its muscle actuator. The controller can be configured to determine a target sensory activity based on a cutaneous sensory map, and, if needed, determine an error in target sensory activity and reaction of the muscle actuator based on the cutaneous sensory map (CSM).

Afferent Cutaneous Feedback Pathway:

1) Contact, pressure, and shear forces applied to the external prosthesis can be measured by intrinsic sensors using, for example, capacitive or resistive sensors located on contact regions (e.g., contact regions 1 through m; for example, as shown with sensors 457 in FIG. 10) of the external prosthesis (1→2, FIG. 26).

2) The cutaneous information of 1 through m contact regions can be converted to target activity level of 1 through m CMI actuators based on a cutaneous sensory map (2→3, FIG. 26).

3) The target activity of m CMI actuators can be implemented by closed-loop control based on state/force sensing from m CMI actuators. First, the current state/force of the m CMI's are measured through implanted sensors, such as by sonomicrometry, magnetic tracking, and electrodes (4→5, FIG. 26). The m CMI errors in the activity of actuators are computed based on the cutaneous sensory map (CSM) and measurements (5→3→6, FIG. 26). These errors can be corrected by functional electrical/optical stimulation on each CMI actuator (6→7→4, FIG. 26). When the state/force sensing is not available for the closed-loop control, the controller can be designed in an open-loop fashion in which the reference for each CMI actuator (6, FIG. 26) is generated based on an open-loop model, such as a look-up table or an inverse model of identified dynamics of the CMI actuator. When a synthetic actuator is used (4, FIG. 26), the same MIC can be applied through the use of a proper motor driver for actuator (7, FIG. 26) and available state measurements of the CSM (5→3, FIG. 26).

4) With the controller described in 3), above, the target contact, pressure, and shear forces can be applied to m innervated skin flaps (4→8→9, FIG. 26). This mechanical stimulus can be converted to neurophysiological afferent cutaneous feedback to the CNS by mechanoreceptors within each skin flap (9→10→11, FIG. 26).

Implementation of the Cutaneous Sensory Map (CSM) for m CMI's:

The CSM can be developed prior to implementation of the MIC by employing a mirroring task. For example, in the case of a person with unilateral amputation, each CMI can be actuated and the corresponding cutaneous sensation of a subject can be accessed by having him/her mirror the cutaneous sensation using their unaffected limb. The mirrored cutaneous sensation can be measurement by, for example, a load cell or FSRs. By creating a look-up table between a given actuation and its invoked sensation, the look-up table can be used as CSM for the MIC. In another example, dynamic modeling based on state/force sensing of m CMI's can be employed (4→5, FIG. 26). By developing a dynamic model between the activity levels of the m CMI actuators to the measured force, the CSM dynamics can be identified for the MIC.

Bi-Directional Control with Afferent Proprioceptive Feedback Between n PMI's and k Joints of an External Prosthesis:

1) The innervated muscle end organ of each PMI can be activated by motor intent and reflex circuits within the CNS (11→12→13, FIG. 26).

2a) The state/force of n PMI end organ muscles are measured by implanted sensors (13→14, FIG. 26). The measurements from each PMI are integrated based on the Virtual Limb Model (VLM) (14→15, FIG. 26). By implementing the VLM (comprising, for example, virtual muscle-tendon dynamics, non-linear biological moment arms, inertia, friction of bone segments, etc.), the net muscular joint torques can be calculated.

2b) The VLM further integrates with positions, speeds and actuator torques of the k DoF external prosthesis (1→16→15, FIG. 26). The external forces applied to k DoF external prosthesis, as well as internal forces such as gravitational and inertial forces, can be simulated with the VLM. Based on the integration of the PMI's and the external prosthetic measurements, the VLM computes the target joint positions, speeds, and torques for k prosthetic joints, as well as target muscle states and forces for PMI's to realize the simulated VLM dynamics.

3) Kinesthetic awareness resulting from n PMI's and the external prosthesis is implemented by controlling the k prosthetic joints, tracking the reference values of position, speed, and joint torques, as well as controlling n PMI muscle states and forces that correspond to those k prosthetic joints. This implements action and reaction relationships between n innervated muscle end organs and k joints based on the VLM, providing the physiological afferent proprioceptive feedback and efferent controllability of the external prosthesis. The bi-directional control can include two closed-loop systems.

A. Implementation of Action and Reaction on n PMI's for Afferent Proprioceptive Feedback:

A1. Current muscle state and force of each PMI actuator is measured by the implanted sensors (17→18, FIG. 26).

A2. 1 through n PMI errors in muscle state and force can be computed by comparing the VLM outputs with the end organ measurements (14, 18→15→19, FIG. 26).

A3. Feedback can be implemented by controlling functional electrical/optical stimulation of each PMI based on the computed errors (19→20→17→21, FIG. 26). Note that when the feedback sensory information from the PMI actuator (18, FIG. 26) is not available due to practical issue of limited space on the PMI, similar tracking performance can be achieved by feedback from the PMI innervated end organ sensory information (14, FIG. 26). When a synthetic actuator is used (17, FIG. 26), the same MIC can be applied by employing a motor driver for the actuator (20, FIG. 26), as well as available state measurements of the VLM (18→15, FIG. 26).

A4. From the control actions applied on the end organ muscles by the actuators (17→21→13, FIG. 26), the muscle end organs' states and forces that correspond to the external prosthetic joint positions, speeds, and torques are then realized. This provides physiological afferent proprioceptive feedback through sensory organs in the innervated end organ muscles of the n PMI's (13→22→11, FIG. 26).

B. Implementation of Action and Reaction on k Prosthetic Joints for Efferent Control:

B1. Current positions, speeds, and actuator torques, as well as all external forces acting on the prosthesis, are measured by the intrinsic sensors of the external prosthesis (1→16, FIG. 26).

B2. These intrinsic measurements are then compared with the VLM outputs and the errors in the joint positions, speeds, and actuator torques are calculated (16→15→23, FIG. 26).

B3. The target joint kinematics and actuator torques are implemented by driving the prosthetic actuators within the external prosthesis based upon the computed errors (23→1, FIG. 26).

Modification of the VLM to Account for Imperfect Preservation of Physiological Capacity in End Organ PMI Muscles and Actuator Capacity of the External Prosthesis:

In practice, there may be a significant degree of PMI muscle reduction in terms of physiological cross sectional area and length caused by the amputation procedure. For example, a portion of the original native muscle may be denervated and be used as the actuator to drive the innervated end organ muscle segment for efferent-afferent signaling. To account for changes in physiological capacities of each end organ muscle, independent scaling factors both in muscle state and force can be defined. The scaling factors can be investigated using the actuator 120 and physiological readings 118, 119 (FIG. 21), identifying muscle properties such as maximum force and stroke length. By defining scaling factors for each PMI as a ratio of measurements to target physiological values used in the VLM, each physiological reading from each PMI can be scaled up or down when it is reflected on the other PMIs and the k DoF prosthesis. Similarly, position, velocity, and external and internal forces applied to the prosthesis, such as gravitational and inertial forces, as well as reaction forces from the environment, can be scaled to meet the physiological capacity of each PMI. Scaling factors for the prosthetic system can be designed to meet the actuator 120 capacity, comfort of the subject, and physiological safety estimates. Further, scaling factors both in joint kinematics and torques can be defined for each joint of the external prosthesis based on the range of motion and joint torque capacity of each actuator. The measurements of intrinsic sensors can be scaled down or up when they are fed to the VLM to meet the hardware specifications of the external prosthesis. Reversely, the reference values from the VLM can be scaled to match the capacity of each actuator of the external prosthesis.

Implementation of the Mechanoneural Interface Controller (MIC) for n PMI's and k Prosthetic Joints with Scaling Factors:

The target control variables for efferent-afferent signaling including muscle length l, muscular force f, joint angle θ, and torque T of n PMI's and k joints of the external prosthesis are computed in this section.

1) Synchronization of Muscle States and Joint Kinematics (l and θ)

The kinematics synchronization of n PMI's and k prosthetic joints can be achieved if the following relationships are satisfied.

$$k_{p1} l_1 = L_1(\theta) \tag{eq. 1}$$

$$k_{p2} l_2 = L_2(\theta) \tag{eq. 2}$$

$$\vdots$$

$$k_{pn} l_n = L_n(\theta) \tag{eq. 3}$$

In the equations above, $k_{pi}$ and $l_i$ indicate the position scaling factor and muscle length of the ith muscle, respectively, and θ indicates the position vector of 1 through k prosthetic joints. $L_i$ refers to the ith muscle length in the VLM domain that drive k prosthetic joints. Equations 1 through 3 show that 1 through n muscles are scaled into each corresponding VLM muscle by the position scaling factors, $k_{pi}$. By setting the target muscle length as an average of each muscle length of each PMI and that of the corresponding VLM muscle length average, the reference values are given as follows.

$$l_1^{ref} = \frac{1}{2}\left(l_1 + \frac{1}{k_{p1}}L_1(\theta)\right) \tag{eq. 4}$$

$$l_2^{ref} = \frac{1}{2}\left(l_2 + \frac{1}{k_{p2}}L_2(\theta)\right) \tag{eq. 5}$$

$$\vdots$$

$$l_n^{ref} = \frac{1}{2}\left(l_n + \frac{1}{k_{pn}}L_n(\theta)\right) \tag{eq. 6}$$

In the equations above, $$l_i^{ref}$$

indicates the target reference of the ith muscle of the ith PMI. Here, the average of each muscle length of the ith PMI and that of the ith corresponding VLM muscle is to allow for position tracking errors in considering the limited actuation capacity of the ith PMI. The strict condition for the kinematic synchronization can be set by simply defining $$l_i^{ref}$$

as $$\frac{1}{k_{pi}}L_i(\theta).$$

Meanwhile, note that the two choices of $$l_i^{ref}$$

converge to the same value when the conditions of kinematic synchronization (eq. 1-3) are achieved. The position controller $c_{pi}$, such as a PID controller, can be built for the ith PMI actuator as follows, where $u_{pi}$ indicates the control input to the ith PMI actuator to achieve a position control.

$$u_{pi} = C_{pi}\left(l_t^{ref} - l_t\right) \tag{eq. 7}$$

2) Synchronization of Muscular Forces and Joint Torques (f and τ)

The synchronization of muscular forces and joint torques of n PMI's and k joints of the external prosthesis can be achieved if the following relationships are satisfied.

$$R_{11}(\theta)k_{f1}f_1 + R_{21}(\theta)k_{f2}f_2 + \ldots + R_{n1}(\theta)k_{fn}f_n + T_1 = Z_1\ddot{\theta}_1 \tag{eq. 8}$$

$$R_{12}(\theta)k_{f1}f_1 + R_{22}(\theta)k_{f2}f_2 + \ldots + R_{n2}(\theta)k_{fn}f_n + T_2 = Z_2\ddot{\theta}_2 \tag{eq. 9}$$

$$\vdots$$

$$R_{1k}(\theta)k_{f1}f_1 + R_{2k}(\theta)k_{f2}f_2 + \ldots + R_{nk}(\theta)k_{fn}f_n + T_k = Z_k\ddot{\theta}_k \tag{eq. 10}$$

$R_{ij}$ and $k_{fi}$ indicate the moment arm and force scaling factor of the ith muscle spanning the kth joint, respectively. $f_i$ and $T_1$ indicate the ith muscular force of PMI and the jth external joint torque of the VLM calculated based on the intrinsic sensor readings, as well as simulated internal forces. When $f_i$ is not directly accessible, the muscle model such as Hill-type model can be used to estimate $f_i$ from h and EMG. $Z_j$ and $\ddot{\theta}_j$ show the impedance and angular acceleration of the jth joint of the VLM. The angular reference $$\ddot{\theta}_j^{ref}$$

of the jth actuator of the external prosthesis is given as follows.

$$\ddot{\theta}_1^{ref} = \frac{1}{Z_1}(R_{11}(\theta)k_{f1}f_1 + R_{21}(\theta)k_{f2}f_2 + \ldots + R_{n1}(\theta)k_{fn}f_n + T_1) \tag{eq. 11}$$

$$\ddot{\theta}_2^{ref} = \frac{1}{Z_2}(R_{12}(\theta)k_{f1}f_1 + R_{22}(\theta)k_{f2}f_2 + \ldots + R_{n2}(\theta)k_{fn}f_n + T_2) \tag{eq. 12}$$

$$\vdots$$

$$\ddot{\theta}_k^{ref} = \frac{1}{Z_k}(R_{1k}(\theta)k_{f1}f_1 + R_{2k}(\theta)k_{f2}f_2 + \ldots + R_{nk}(\theta)k_{fn}f_n + T_k) \tag{eq. 13}$$

When a reliable angular acceleration of each joint can be provided directly, each actuator of the external prosthesis can be driven based on an acceleration control. However, generally, acceleration feedback suffers from large noise and phase delay due to second order derivatives. Here, the joint torque reference is calculated for torque control using the inherent dynamics of the jth joint of external prosthesis $J_j$, as shown below, to enable current feedback control.

$$\tau_1^{ref} = \frac{J_1}{Z_1}(R_{11}(\theta)k_{f1}f_1 + R_{21}(\theta)k_{f2}f_2 + \ldots + R_{n1}(\theta)k_{fn}f_n + T_1) \tag{eq. 14}$$

$$\tau_2^{ref} = \frac{J_1}{Z_2}(R_{12}(\theta)k_{f1}f_1 + R_{22}(\theta)k_{f2}f_2 + \ldots + R_{n2}(\theta)k_{fn}f_n + T_2) \tag{eq. 15}$$

$$\vdots$$

$$\tau_k^{ref} = \frac{J_k}{Z_k}(R_{1k}(\theta)k_{f1}f_1 + R_{2k}(\theta)k_{f2}f_2 + \ldots + R_{nk}(\theta)k_{fn}f_n + T_k) \tag{eq. 16}$$

Highly accurate system identification of $J_j$ can be conducted based upon standard system identification procedures. The torque controller $C_{\tau j}$, such as a PID controller, can be built for the jth actuator of the external prosthesis as follows, where $U_{\tau j}$ is the control input to the jth actuator of the external prosthesis for torque control.

$$U_{\tau j} = C_{\tau j}\left(\tau_j^{ref} - \tau_j\right) \qquad \text{(eq. 17)}$$

Similarly, the target acceleration of the ith PMI muscle length $$\ddot{l}_i^{ref}$$

is defined as follows.

$$\ddot{l}_i^{ref} = -\dot{R}_i(\theta)\dot{\theta} - R_i(\theta)\ddot{\theta} \qquad \text{(eq. 18)}$$

$R_i(\theta)$ is a matrix consisting of the moment arms of the ith muscle of the 1 through k joints for the VLM defined as follows.

$$R_i(\theta) = \mathrm{diag}(R_{i1}(\theta), R_{i2}(\theta), \ldots, R_{ik}(\theta)) \qquad \text{(eq. 19)}$$

Similarly, when reliable acceleration information for each muscle can be provided directly, each PMI actuator can be driven based on acceleration control. However, generally, acceleration feedback suffers from large noise and phase delay due to second order derivatives. Here, the muscle force reference is calculated for force control using the inherent dynamics of the ith PMI $M_i$ as shown below to enable force feedback control.

$$f_i^{ref} = M_i \ddot{l}_i^{ref} \qquad \text{(eq. 20)}$$

Then, force control $C_{fi}$ can be implemented for each PMI.

$$u_{fi} = C_{fi}\left(f_i^{ref} - f_i\right) \qquad \text{(eq. 21)}$$

In the equation above, $u_{fi}$ indicates the control input to the ith PMI's actuator for force control.

3) Hybrid Control of Muscle Force and Length of n PMI's

To implement a high degree of kinesthetic sensation, a hybrid control of force and position is preferred. Therefore, here, a hybrid control for the ith PMI actuator is defined as follows, where $u_{\Sigma i}$ refers to the total control input to the ith PMI for kinesthetic feedback.

$$u_{\Sigma i} = u_{pi} + u_{fi} \qquad \text{(eq. 22a)}$$
$$= C_{pi}\left(l_i^{ref} - l_i\right) + C_{fi}\left(f_i^{ref} - f_i\right) \qquad \text{(eq. 22b)}$$

Because high fidelity control performance can be achieved for mechanical actuators of the k prosthetic joints compared to the n PMI actuators, the torque controller (eq. 17) provides a sufficient degree of kinesthetic response.

4) Modification of the VLM for Full Hybrid Control of Force and Position

To further improve the hybrid control of a k joint external prosthesis, the VLM requires modifications. The hybrid control of the external prosthesis is challenging due to redundancy between the linear muscle space and the external prosthetic joint space; knowing a specific muscle length does not result in a unique set of joint positions. For bi-articular muscle lengths such as, for example, the gastrocnemius (GAS) muscle, the length is a function of multiple joint angles such that unique target joint angles cannot be computed from a given muscle length measurement. Also, some muscles referenced as mono-articular muscles are actually functions of multiple joints such as, for example, the tibial anterior (TA) where its length is a function of both the ankle and subtalar joint angles. However, with some modifications of the VLM, hybrid control for the k joint external prosthesis can be implemented. For such muscles, the dynamics of muscle length in the VLM can be simplified by assuming that primarily the major spanning joint, such as the ankle joint in the case of the TA, determines its dynamics. This allows one to back calculate the corresponding joint angle $\theta_{ij}$ from the given muscle length.

$$\theta_{ij} = L_{ij}^{-1}(k_{pi}l_i) \qquad \text{(eq. 23)}$$

In the equation above, $$L_{ij}^{-1}$$

indicates the inverse function of the ith muscle length to joint angle. For a bi-articular muscle, a cost function can be defined as the minimization of the total joint angle errors to back calculate multiple joint angles.

$$\{\theta_{ij}\} = G_{ij}^{-1}(k_{pi}l_i) \qquad \text{(eq. 24)}$$

In the equation above, $$G_{ij}^{-1}$$

refers to the cost function for back calculation of multiple joint angles $\{\theta_{ij}\}$.

$$G_{ij}^{-1}$$

can be used also for mono-articular muscles to substitute $$L_{ij}^{-1}$$

Then, the references of the jth target joint angle $$\theta_j^{ref}$$

can be calculated as follows.

$$\theta_j^{ref} = \frac{1}{N+1}\left(\sum_{i=1}^{N}\theta_{ij} + \theta_j\right). \qquad \text{(eq. 25)}$$

Here N is the number of muscles of then PMI's that span the jth joint of the VLM. $\theta_{ij}$ is the back calculated jth joint angle from the ith PMI muscle based on eq. 23 and eq. 24. Then, the position control for the jth joint $C_{Ji}$ can be implemented as follows, where $U_{Ji}$ is the control input to the jth actuator of the external prosthesis for position control.

$$U_{Ji} = C_{Ji}\left(\theta_j^{ref} - \theta_j\right) \qquad \text{(eq. 26)}$$

Therefore, the hybrid control of the jth joint of the external prosthesis can be implemented as follows, where $U_{\Sigma i}$ refers to the total control input to the jth actuator of the external prosthesis.

$$U_{\Sigma j} = U_{ji} + U_{\tau j} \qquad \text{(eq. 27a)}$$

$$= C_{Ji}\left(\theta_j^{ref} - \theta_j\right) + C_{\tau j}\left(\tau_j^{ref} - \tau_j\right) \qquad \text{(eq. 27b)}$$

Based on the modification of the VLM, the $$I_i^{ref}$$

of eq. 7 can be also modified as follows, where $l_{ij}$ is the computed muscle length of the ith muscle from the jth muscle from their back calculated joint angles.

$$I_i^{ref} = \frac{1}{N+1}\left(\sum_{j=1}^{N}\frac{k_{pj}}{k_{pi}}l_{ij} + \frac{1}{k_{pi}}L_i(\theta)\right) \qquad \text{(eq. 28)}$$

The full hybrid control of both n PMI's and k joints of the external prosthesis (eq. 22 and 27) provides the improved kinesthetic response based on the modified VLM and assumed cost function (eq. 23 and 24). Note that if the control designer prefers not to modify the VLM and assume any cost function, the hybrid control of n PMI's and the torque control of the external prosthesis can still provide high kinesthetic controllability (eq. 21 and eq. 22) as described in 3) above.

EXEMPLIFICATION

Example 1. Evaluation of CMIs

The neuromechanical properties of a CMI were evaluated. It was hypothesized that muscle placed in a circumferential architecture can generate normal forces on skin that are sufficient to activate skin receptors. It was further hypothesized that muscle actuation can be modulated to generate graded touch sensations and various modes of vibration. It was anticipated that an array of stimulation modes will independently and simultaneously activate SA and RA receptors. To test these hypotheses, surgery was performed on a murine animal model using a skin graft harvested from the medial aspect of the right hind limb on its saphenous nerve pedicle (FIGS. 6A-6D). The extensor digitorus longus (EDL) was harvested, positioned in a cuff-like fashion around the skin graft, and innervated with the transected peroneal nerve. After six weeks, electrophysiological, mechanical, and histological testing was performed to evaluate the functionality of the CMI.

Figure 11:
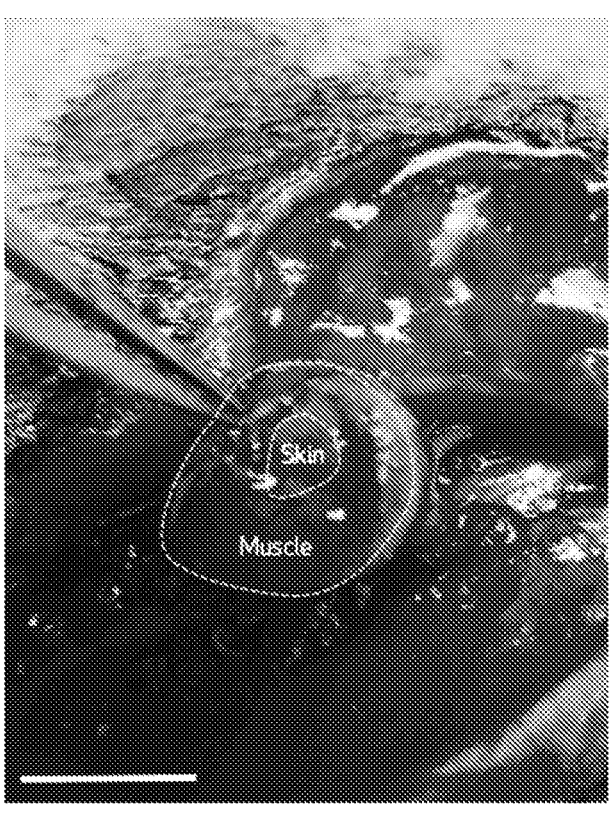
FIG. 11 is an image of a cross-sectional view of a murine model CMI at harvest, which demonstrates clear margins between the muscle actuator and the skin.

CMI's were constructed by wrapping an EDL free muscle flap innervated with the peroneal nerve around a pedicled, de-epithelialized skin flap in the medial hind limb (FIGS. 6A-6D). Tensions of the muscle and positioning of the skin flap were carefully designed and optimized (see Methods for details). At terminal harvest (FIG. 6D, FIG. 11), the gross morphology of the CMI was evaluated through layer-by-layer dissection under a microscope to assess the healing and remodeling of the tissue. By preserving the vascular supply of both the skin and muscle flaps, we aimed to prevent necrosis and preserve tissue volumes. In all cases, the CMI's healed without any surgical complications and no evidence of necrosis was present. Clear margins demarcating the skin from the muscle and the CMI from surrounding tissues were present and adhesions between the muscle and skin layers had formed, promoting efficient mechanical transfer of muscle actuation to the skin. The composite tissue was supplied by new blood vessels that enabled a healthy nutrient exchange. A thin layer of scar tissue surrounding the construct allowed lubricious sliding and movement. Though the muscle and skin underwent modest atrophy (20%), tensions of the muscle actuator remained efficacious.

Characterization of the Electromechanical Properties of the CMI

Figure 6E:
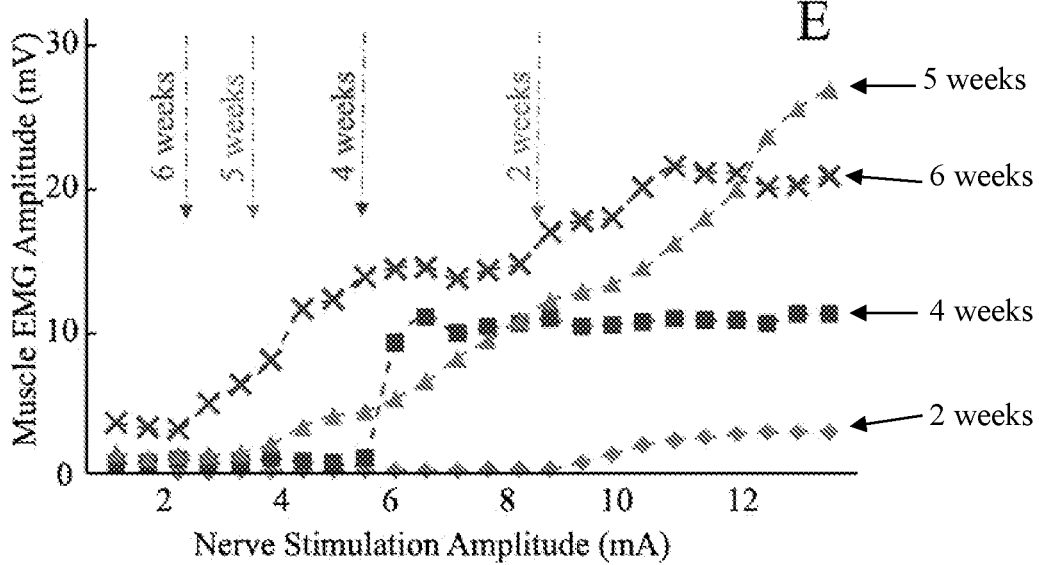
Figure 6F:
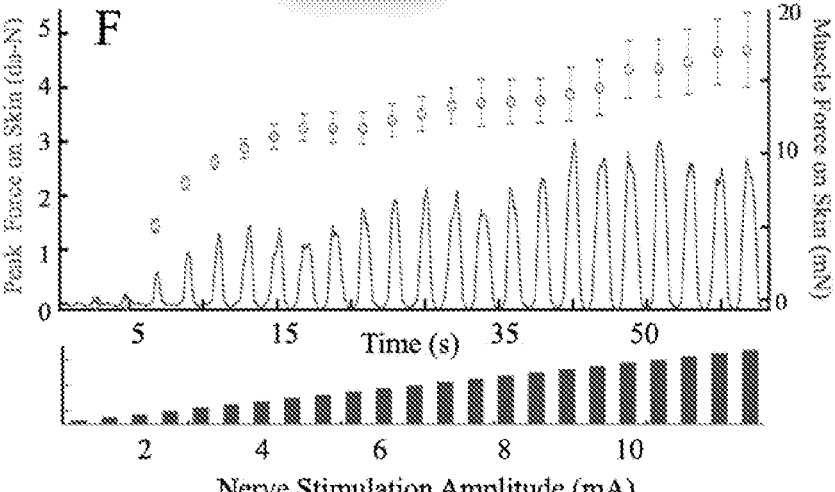
Figure 7A:
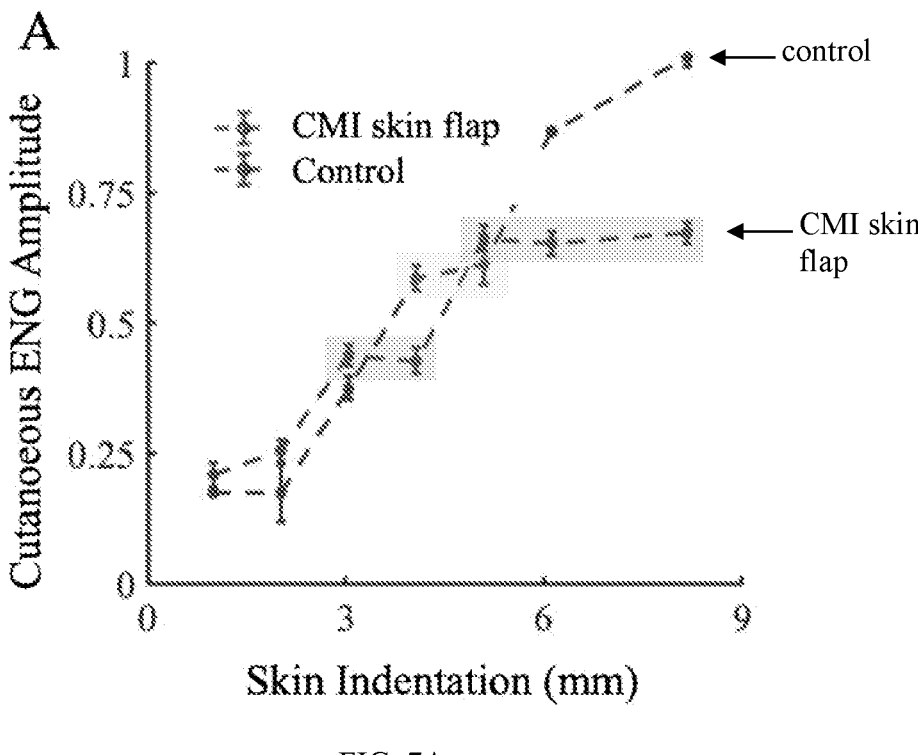
FIGS. 7A-7D illustrate afferent response results of a murine model CMI.
Figure 7B:
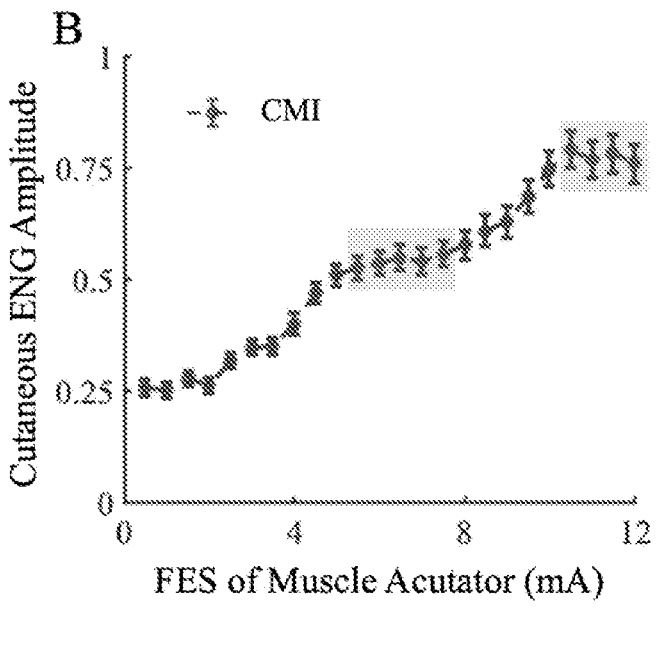
Figures 7C, 7D:
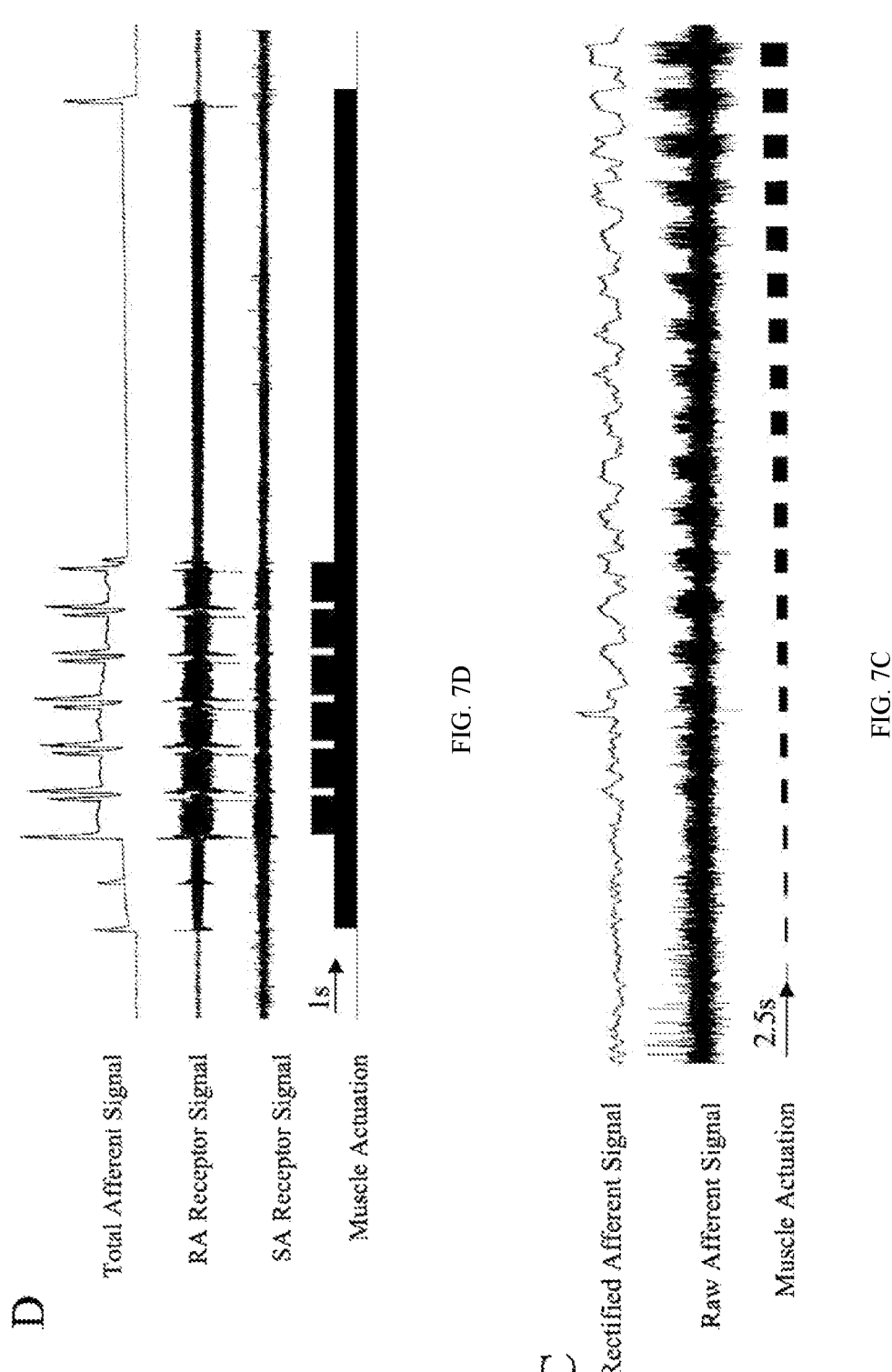
Figure 12:
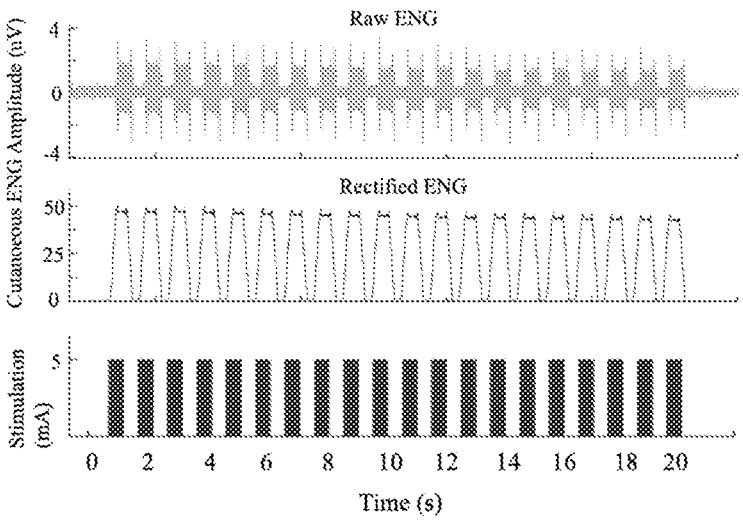
FIG. 12 is a graph of fatigue response results of a murine model CMI to repeated actuation. The muscle was repeatedly actuated with 5 mA of electrical stimulation (bottom section). Raw and rectified ENG recordings demonstrate consistent production of afferent signal and a decrease of less than 15% magnitude over the 20 second course of actuation.

Each week, muscle grafts were electrically stimulated on the innervating nerve to assess reinnervation and elicit contraction of the skin flap. During weeks two and four, the average rate of spontaneous fasciculations in the muscle graft during a 90 second recording interval decreased from three to zero, indicating reinnervation of the muscle graft. Corroborating the reinnervation, a decrease in the minimum threshold for muscle activation (indicated by dotted lines in FIG. 6E) was observed over time. At six weeks, the CMI was electrically stimulated (0.5 mA-12 mA) to characterize the electromechanical capabilities of the muscle actuator. The EMG response of the muscle graft (FIG. 6E) graded with increased stimulation until saturating levels were reached. Tetanic contractions were elicited at 2 mA after six weeks. Similar measurements were performed in the contralateral limb and tetanic contractions were elicited at 2 mA. The measured actuation forces generated in the inward direction, normal to the muscle striation, graded with stimulation, with 3 peak forces ranging between 2 and 4.5 mN (FIG. 6F). Repeated contractions were elicited with less than 13% fatigue over the course of 20 seconds, suggesting substantial durability of the CMI for use in repetitive tasks (FIG. 12). Graded Afferent Signal Generation in Response to Static Touch The CMI was actuated with a variety of stimulation parameters mimicking static touch to assess its ability to produce graded afferents representing contact forces at increasing magnitudes. To derive a baseline of natural afferent signaling, the medial skin surface of the contralateral limb was indented using a mechanical arm, while afferent signals were recorded from the saphenous nerve that innervated that dermatome. This control data demonstrated a gradation in ENG amplitude in response to increasing indentations. The CMI was also mechanically indented and afferent responses from the cutaneous nerve were generated with similar latencies, magnitudes and gradation as compared to the controls (FIG. 7A). The normalized afferent signal values ranged from 50 to 800 uV for indentations of 1 mm to 9 mm in both controls and CMI's. Then, the CMI was electrically stimulated to induce muscle contraction, while recording afferent signals from the cutaneous nerve (FIGS. 7B, 7C). The afferent response demonstrated explicit gradation with strong signal-to-noise ratios at stimulation amplitudes greater than 2 mA and no de-sensitization with repeated stimuli (FIG. 7C). Stimulation at 12 mA produced strong and maximal contractions of the skin flap.

Distinct Mechanoreceptor Response to Muscle Actuation

Rodent skin possesses mechanotransducers that are very similar in function and adaptation rates to human skin. Maintenance of function and selective activation of these receptors are critical features of the CMI. Thus, individual receptor activation, saturation, and simultaneous firing capabilities were compared through electrophysiological testing.

Receptor saturation is an indicator of the dynamic range of the Merkel and Ruffini-type cells and defines the overall sensitivity of the CMI. Afferent receptor saturation occurs when increasing levels of stimulation produce statistically insignificant differences in ENG magnitude (student's t-test, p<0.05). During the graded mechanical stimulation trials receptors saturated between 3 and 4 mm and above 5 mm in the CMI. In controls, saturation occurred between 4 and 5 mm indentations (FIG. 7A). The modest shifts in CMI saturation ranges are attributed to the mechanical changes in elasticity and scarring that occur as a result of its placement inside the limb. Under electrically stimulated muscle actuation, receptor saturation was observed at stimulation amplitudes greater than 10 mA, with an intermediary plateau between 6 and 7.5 mA (shaded boxes). The two plateaus in afferent response suggest that the CMI is sensitive to stimuli until all low-level Merkel receptors are saturated. Then, further stimulation engages additional Ruffini-type receptors, until they have also been saturated. The similarity in trend, response range, and saturation ranges between the mechanically stimulated (FIG. 7A, control) skin and electrically stimulated CMI (FIG. 7B) demonstrates that the electrically-stimulated muscle actuator is able to mimic the action of a mechanical indenter and elicit similar responses to static touch. A representative trial is presented in FIG. 7C, which demonstrates the production of afferents for each given level of muscle actuation. To verify that the afferents were generated by mechanical actuation, and not direct electrical activation, uncoupled the muscle was uncoupled from the skin and electrical stimulation was performed. Even at the highest current intensities, afferents were not recorded from the skin flap (FIG. 7C).

To discern the capacity for the CMI to independently engage both slowly SA and RA receptors, a patterned stimulation test was performed. Electrical stimulation created sustained indentation with periodic pulsed vibrations and deeper indentation in the muscle (muscle actuation, FIG. 7D). Recordings from fine wire electrodes implanted in different fibers demonstrated signals from both SA and RA receptors (FIG. 7D). The SA receptor signal, characteristic of Merkel and Ruffini cells, demonstrates heightened strength during indentation with a slow decay rate, reaching baseline only after stimulation has ceased. The RA receptor, characteristic of Meissner and Pacinian corpuscles, demonstrates spiking during onset and offset of stimuli, with a quick return to baseline (FIG. 7D). These signals were similar in adaptation rate and onset dynamics as those recorded from the controls. This suggests that the CMI is able to simultaneously activate static touch, vibration, and dynamic touch receptors. Thus, the CMI is capable of activating distinct receptors in a physiological manner to convey complex sensations that involve more than one type of touch.

Afferent Signal Generation to Vibratory Actuation

Figure 8A:
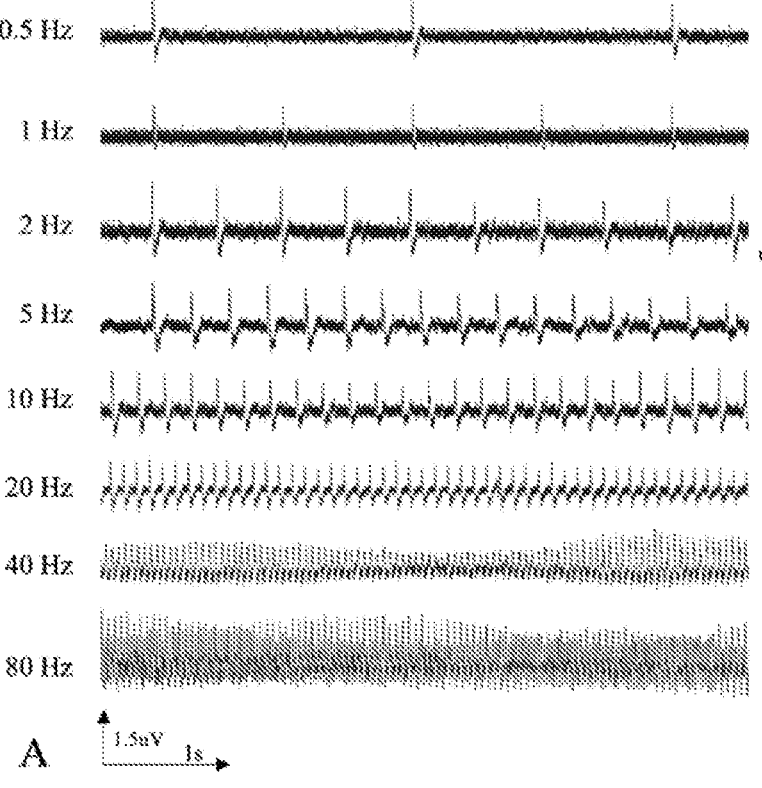
FIGS. 8A-8B illustrate afferent response results of a murine model CMI to vibration.
Figure 8B:
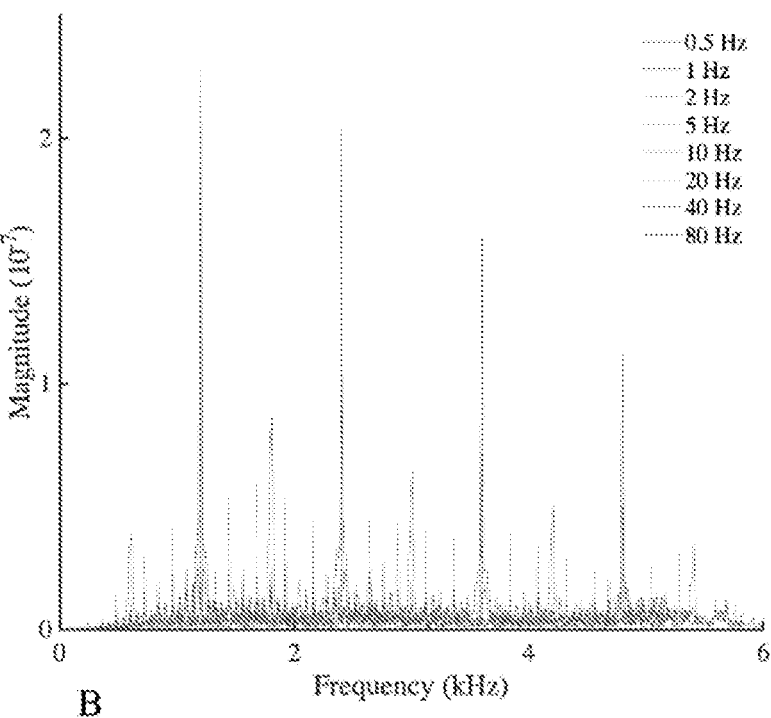

The CMI was actuated at various frequencies to assess the ability of the CMI to transduce vibratory sensation. Prior studies have utilized phase locking consistency (1 afferent impulse produced for 1 vibration) as a metric to evaluate the ability of skin to generate uniquely patterned codes for each frequency (50-400 Hz in glabrous skin). Frequencies of muscle actuation between 0.5 Hz and 80 Hz were induced and the afferent response was recorded. Vibrations above 80 Hz were not able to be actuated given the electrochemical coupling properties, damping, and fatigability of muscle. A representative example of the response to each frequency is shown in FIGS. 8A, 8B. The CMI's afferent response followed frequencies of stimulation between 0.5 Hz to 80 Hz, and readily phase locked to frequencies greater than 10 Hz. Coherence analyses between the resulting afferents demonstrated no statistical similarity, even at a threshold of 0.75. The heightened sensitivity to higher frequency vibration in CMI is consistent with the anatomical functionality of the CMI. De-epithelialization of the flaps likely resulted in a loss of low frequency sensors such as Meissner corpuscles and thus a greater proportion of high frequency sensors were present in the deeper dermal layers. These results demonstrated that the CMI is able to uniquely distinguish vibratory sensations for at least 8 frequencies.

CMI Fatiguability Enables Chronic Use

Following 15 minutes of intermittent stimulation, a six second burst of 40 Hz stimulation was applied to the muscle graft to quantify its fatigue rate. Amongst the seven animals, between 86-92% of the original RMS EMG was achieved at the end of the 6-second period. A representative trial is provided in FIG. 13. This fatigue rate was consistent with that of the contralateral EDL. The indwelling localization of the skin flap may change the sensitivity of mechanical pain, and LTMR receptors. To characterize potential changes to the nociceptive threshold, calibrated forceps were used to apply forces on the CMI. Sensitivity thresholds were compared to that of the same skin flap in animals receiving the same surgery. No significant hypo- or hyper-sensitivity was found in the CMI group (p=0.69, 2-tailed t-test) (See Supplemental Materials for detailed methods and FIG. 14).

Histology Demonstrates Viable Composite Tissue

Figure 9A:
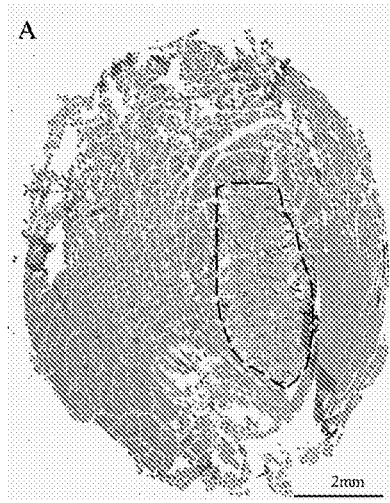
FIGS. 9A-9G illustrate histological analysis of a murine model CMI.
Figure 9B:
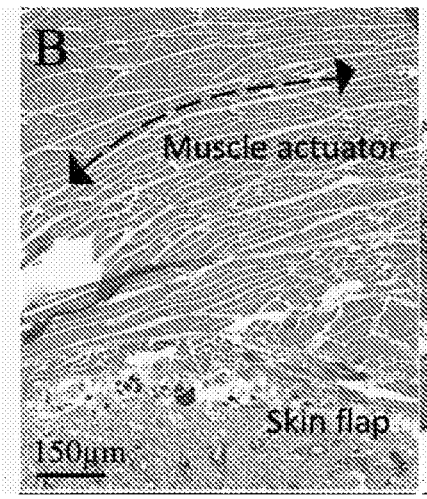
Figure 9C:
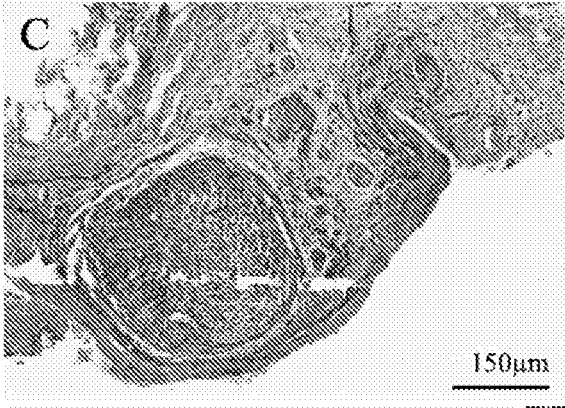
Figure 9D:
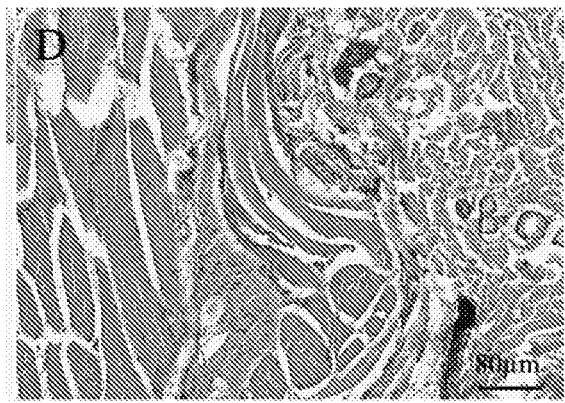
Figure 9E:
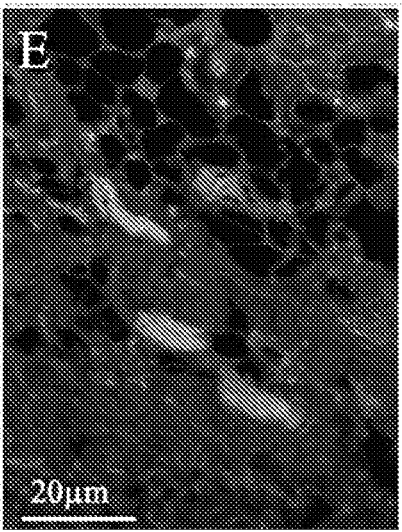
Figure 9F:
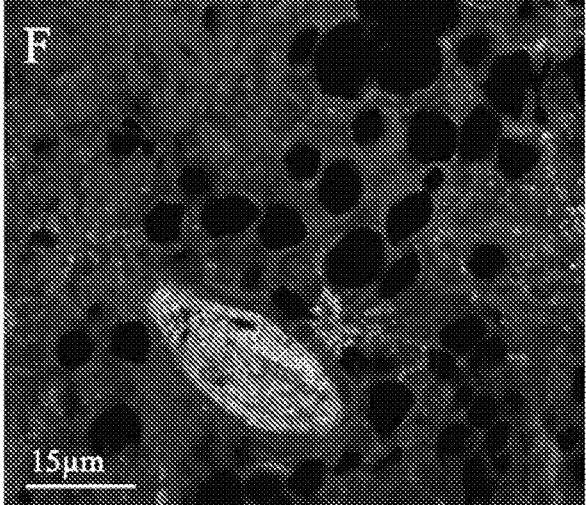
Figure 9G:
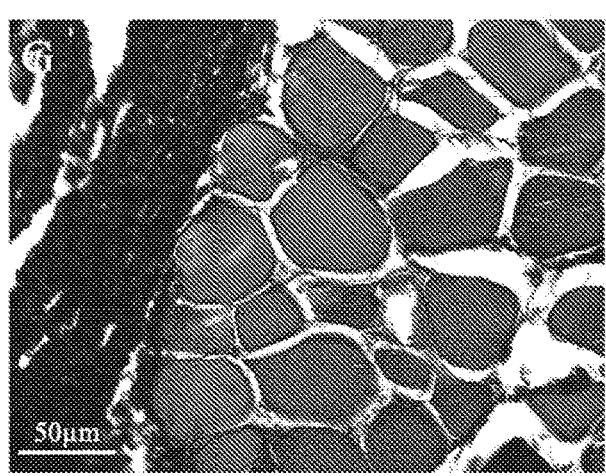

The CMI, surrounding tissues, and the skin from the contralateral side were harvested, processed, and sectioned to compare the cell and tissue level structures present in the CMI and control skin, as well as to determine the extent of adhesion and remodeling of the composite tissue. In FIG. 9A, the cross section of the CMI demonstrates the healthy skin flap being circumferentially encompassed by the muscle actuator with robust myocytes. While this slice of the CMI indicates an approximately 1:4 ratio of skin to muscle, the average diameter of the skin flap at its largest section yielded a 1:3 ratio of skin to muscle. The fibers of the muscle actuator were oriented in a length-wise fashion around the skin flap, enabling maximal transfer of muscle actuation forces (FIG. 9B). Numerous cutaneous nerves, ranging in size, were found to innervate the skin flap in the epidermal layers (FIG. 9C, FIG. 15). The presence of these nervous structures supports the range of afferent signals recorded through electrophysiology. Additionally, numerous blood vessels were found in both the muscle and skin layer, including newer vessels. The interface between skin and muscle showed healthy integration and bundling collagenous adhesions near suture sites (FIG. 9D), indicating that the minimally manipulative surgical method was sufficient to create a composite tissue structure through natural healing processes. Merkel cells and Meissner corpuscles were identified in the epidermal layer (FIGS. 9E, 9F) through immunohistochemical staining for s100, demonstrating healthy morphologies. These corroborate a mechanotransducive basis for the specific touch and vibration sensations that were captured by the CMI. Significant adhesion occurred between the skin graft and muscular actuator as evidenced by the dense connective tissue lining the graft in a trichrome stained cross section of the CMI (FIG. 9G). Together, the histological analyses indicated that the CMI had reinnervated and revascularized as a composite tissue with the intended architecture and was able to relay neural signals through native mechanotranduscers present in the dermal layer.

The cutaneous mechanoneural interface (CMI) provides a new system to generate natural cutaneous feedback from neuroprosthesis for persons with limb amputation. Given the prominent role of cutaneous feedback and its inherently complex nature, natural biological tissue was leveraged in a new surgical architecture to actuate, transduce, and transmit the cutaneous sensations from an external prosthetic limb. In the presented experiments, the CMI is constituted by an electrically activated muscle mechanically coupled to a natively innervated skin flap where controlled strains are applied to the flap eliciting an afferent response. Through an empirical study, a map of the neurophysical properties and dynamics of electrical stimulation-based muscle actuation in the CMI and the resulting afferents was developed. Muscle actuation successfully evoked graded afferent responses characteristic of both SA and RA receptors and static touch and vibration distinctly. At least four distinct magnitudes of static touch and over eight frequency modes were discerned by the CMI. Afferent responses and adaptation to stimuli were consistent with the response evoked on the contralateral side as well as established studies in murine models. Thus, with a combinatorial stimulation manifold, segments of natural sensations were recreated in the CMI that were comparable to that of the natural cutaneous response in terms of signal patterns. Throughout the course of experimentation, the muscle of the CMI contracted with consistent and repeatable force output and minimal fatigue in all animals.

Given that current commercial prosthetic systems offer no cutaneous feedback, sensation of single digits in the hand or the four major pedicles of the plantar surface of the foot represents a major advance and stands to offer significant benefit to patients. Notwithstanding, a limitation of the current CMI model is the spatial resolution of cutaneous feedback, which can only be scaled up to the extent of fascicular dissection or the number of independently pedicled skin flaps. Numerous muscle cuffs can be positioned on a given skin flap to actuate separate spatial regions (FIG. 17) and microfabricated actuators capable of high spatial resolution may be used in place of biological actuators. Further, in the current model, vibration and contact are the primary forms of actuation facilitated by the cuff architecture. Alternative CMI architectures to enable additional modes of sensation were investigated during the initial phases of this study (see Alternative CMI Architectures and FIGS. 16A-C). These geometries, including the 1) subcutaneous actuator (n=3), 2) sandwich actuator (n=3), and 3) conical actuator (n=3) architectures, should be further investigated and incorporated in future models.

Murine skin is considered a translational model for reconstructive and neurophysical approaches. Previous studies utilizing similar reinnervated muscle grafts for neural recording have made their translation directly from rat to human. In a similar vein, the results of this study were found to be immediately applicable to the human case.

Translation

The CMI can be readily translated to the clinic in conjunction with existing and emerging technologies that facilitate percutaneous communication, prosthetic sensorization, and implantable tissue stimulation. A number of sensorized prostheses being developed in the research setting possess the capability to provide exteroceptive information including hardness, roughness, temperature, pressure and shear information from tactile sensors. Notably, the modular prosthetic limb (MPL) developed by the Applied Physics Laboratory (APL) features fingertip sensors that can measure pressure, shear, fine point contact, temperature/heat flux, and vibrations. Additionally, a few sensorized prostheses are commercially available, including the VariPlus Speed, and SensorHand Speed by Ottobock. The SensorHand Speed embodies stain gauges in the thumb, force sensors on the fingers, and a bend sensor to measure hand aperture to adjust grip strength and minimize slippage. To convey tactile information and ground contact forces, SensArs is developing the Sensy artificial skin.

Across the prosthetics field, piezo-resistive and conductive sensing are the most common approaches to detecting exteroceptive information, and have been used to determine the difference between various surfaces and pressures encountered by the prosthetic hand. Other researchers have used a multilayered electronic dermis (e-dermis) along with a neuromorphic interface to provide HTMR feedback. To date, information from these sensors has been communicated to a user through peripheral nerve stimulation (PNS), with the limitations described previously. The CMI can be readily paired with these sensorized prostheses, and an electrical stimulation can be implemented using a wireless communication system or a directly wired approach using osseointegrated conduits (FIG. 10). Given the small footprint of each CMI, during amputation, one CMI can be created for each sensory area of importance. In the upper extremity, the distal phalanx of the index, thumb, middle fingers, palm, ring and pinky fingers can be prioritized, in that order. In the lower extremity, the forefoot region, heel pad, digital pads, and arch can be prioritized, in that order. In cases where skin grafts need to be used, the benefit of CMI functionality can be evaluated against the loss of sensation at the donor site.

The course of the CMI's healing and functioning presents few risks as inadequate healing or excessive scarring would only result in the CMI degeneration into benign scar tissue, potential neuroma prophylaxis, and relatively little negative sequelae for the patient. A considerable volume of work indicates that electrical stimulation protects denervated muscles against atrophy, muscle fiber type differentiation, and preserves the contractile and morphological properties. Thus, with regular stimulation of the muscle cuff, no degeneration of the CMI is anticipated, prohibitive to its function. Further revascularization of the CMI is expected to follow the robust regenerative process witnessed for small free tissue flaps in both animal and human models. In this study outlined here, the muscle actuator was vascularized through (1) plasmatic imbibition, (2) inosculation and capillary ingrowth, and (3) large vessel angiogenesis. Additionally, the innervating nerve was accompanied by a blood vessel which supplied the muscle. Thus, when scaling to numerous CMI's within a residual limb it is not expected that micro-fabrication, or transfer of blood vessels, would be necessary. Given these parameters, a multitude of CMI's can be created in the residual limb with no hindrance to limb shape or socket fit. In regenerative cases where skin flaps are grafted on transected cutaneous nerves, the skin acts as a transducer to the native cutaneous nerve and will perform signaling for the original somatotopic region. In cases where cutaneous nerve fascicles pertaining to the prosthetic sensors of priority are unavailable, stimulation-based training may enable neuroplastic reorganization. Other considerations, including operative time, complexity, and compliance with rehabilitation can play a role in patient eligibility and implementation.

In summary, it was demonstrated that the CMI is a new composite tissue capable of recreating and conveying physiological afferent sensation. The strategic combination of accepted surgical techniques from the reconstructive, plastics, and neurosurgery fields employed for the construction of the CMI lends itself to rapid translation. Unlike prior approaches, by reengineering the lost end-organ with natural mechanotransducers, CMI's actuate receptor ensembles at time scales and in configurations that are physiologically natural. Paradigmatically, reengineering end-organ tissues presents a conceptual advance that can be applied to a broad array of challenges in neuromuscular disease, organ transplantation and limb loss. Towards the advancement of neural prostheses for limb loss, it is our view that the CMI may offer patients a more genuine neuroprosthetic sensory experience.

An objective of the study was to assess the ability of a CMI to function as a composite tissue, generating and relaying afferent feedback in response to stimulation. Surgery was performed in a murine model and evaluated outcomes at a 6-week time point. All animal experiments were conducted under the supervision of the Committee on Animal Care at the Massachusetts Institute of Technology (MIT) on 6-month-old Lewis rats, weighing between 450 and 500 g.

Surgical Procedure to Construct CMI's

Rats (n=7) were anesthetized with 1% to 2% isoflurane and premedicated with slow release buprenorphine (1 mg/kg).

Figure 18:
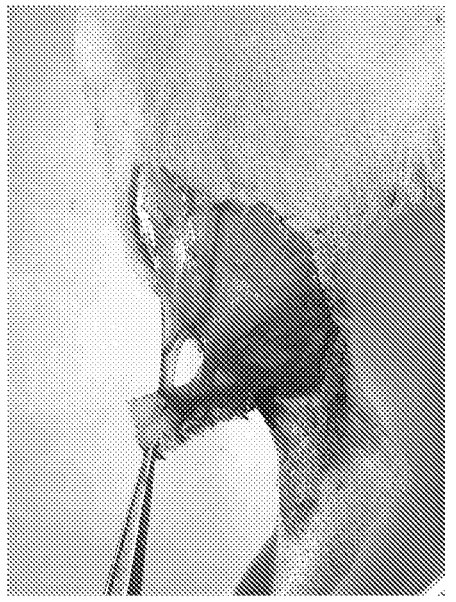
FIG. 18 is an image illustrating isolation of a skin flap. Skin on the medial hind limb was carefully isolated while preserving the neurovascular leash, which is visualized through the fascia in this photograph.

Surgical Procedure to Construct CMI's: Identification and Isolation of a Skin Flap An autologous hairy skin flap was utilized from the rat's hind limb in this study. Harvesting glabrous skin from the foot soles was deemed impractical in the animal model as it would lead to severe morbidity. A linear incision was made on the medial aspect of the right hind limb and blunt dissection was used to identify the saphenous nerve. Distal branches of the saphenous nerve that directly innervate the skin were found and a full thickness flap with a 0.5 cm radius around the point of innervation was isolated (FIGS. 6A and 18). Care was taken to preserve the neurovascular leash and microvasculature supplying the flap. In the human model, any embedded skin flap would be de-epithelialized to prevent cyst formation or folliculitis. Thus, to mimic that procedure, the flap was then de-epithelialized.

Surgical Procedure to Construct CMI's: Preparation of Muscle Graft

The extensor digitorus longus (EDL) was isolated from the anterior compartment of the leg and measured from end to end under resting tension. The EDL was then harvested through transection of the tendons at the origin and insertion (FIG. 6B). The peroneal nerve was transected at its distal junction to the tibialis anterior. A small 0.2 mm cavity was created in the EDL and the epineurium of the peroneal nerve was sutured inside that cavity with 8-0 nylon microsuture. The cavity was then closed with two knots using 8-0 nylon microsuture.

Surgical Procedure to Construct CMI's: Construction of CMI

The anterior compartment was then closed in layers using 4-0 braided suture. The skin flap was folded in half to protect the innervating nerve and expose the dermal side to the muscle graft. The EDL was then placed on the medial fascia and positioned around the skin flap in a cuff like manner, ensuring the maintenance of physiological tension, as previously measured, to create the CMI (FIG. 6C). Excess length of muscle was overlapped to increase actuator volume without compromising the ring tension. 4-0 suture was used to suture the muscle fibers to each other. One suture was used to secure the cuff of muscle to the skin. The construct was sutured to the medial fascia, with care to ensure that the neurovascular pedicle underwent no tension even when the hind limb was stretched. The area was irrigated and the incision closed in layers with 4-0 mono-filament.

Tracking Reinnervation

Muscles are generally silent when healthily innervated. The presence of spontaneous action potentials and fascicles is used diagnostically to indicate incomplete innervation. Every two weeks, bipolar needle electrodes (Natus, 30 G) were subcutaneously placed intramuscularly and the baseline electrical signal was recorded for 3 minutes. The frequency of abnormal spiking was quantified to yield a measure of reinnervation.

To test the full range of muscle activation, the muscle was stimulated with electrical pulses (Frequency: 40 Hz, Amplitude: 0.5-12 ma) and the resulting EMG was measured. Signals were digitally bandpass filtered, rectified and integrated. Thresholds for EMG production were monitored over time to characterize the progression of reinnervation.

Electrophysiology

At 4 and 6 weeks, electrophysiology was performed on the surgically exposed construct to characterize the afferent signal response to varying stimulation parameters. The peroneal nerve innervating the muscle graft was transected to prevent the transmission of afferent musculotendinous signals or electrical noise. Bipolar needle electrodes were placed in the muscle graft and biceps femoris to record the EMG signal and electrical artifact in surrounding tissues. Drops of mineral oil were placed in the area surrounding the construct and cutaneous nerve to insulate the recordings from electrical noise. A ground electrode was placed in the subcutaneous tissue of the back. A hook electrode on the peroneal nerve innervating the muscle graft or an epimysial electrode on the muscle actuator was used to stimulate the graft. A fine wire and hook electrode were placed in/around the saphenous nerve to record afferent signals generated by the skin flap. A fine wire electrode was also placed intrathecally in the L3-L4 junction, and verified by the tail flick reaction. All stimulation was carried out via an IZ2 stimulator and recording was carried out on a Rz5D Base processor and PZ5 neurodigitizer amplifier from Tucker-Davis Technologies.

Figure 19:
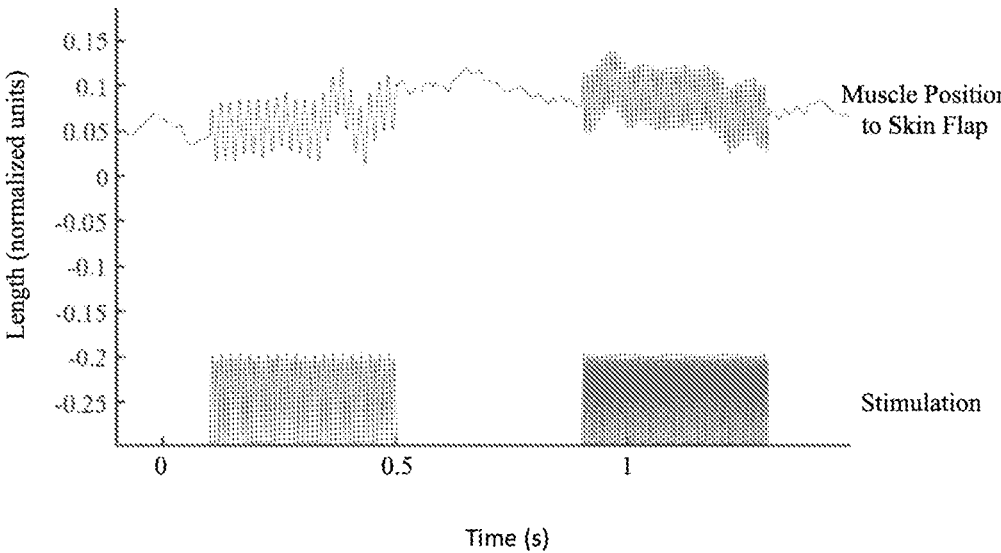
FIG. 19 is a graph illustrating vibratory actuation results of a murine model CMI. Electrical stimulation (bottom section) induced oscillatory contractions from the muscle (top section), which induced a vibratory effect on the skin. A segment from a representative trial is presented.

The CMI was stimulated using electrical pulses of varying frequencies and amplitudes (frequencies: 0.5, 1, 2, 5, 10, 20, 30, 40, 50, 60, 70, 80, 100 Hz; amplitudes: 0.5 mA-12 mA in 0.5 mA increments) to assemble an array of sensations consisting of graded pressure and vibration at different frequencies. For vibratory stimuli, electrical stimulation parameters were optimized until the force recorded from the muscle represented the desired vibration frequency (FIG. 19). Stimulation beyond 12 mA was deemed to be unsafe as it could cause heating and burn the tissue. A pattern of indentation and vibration was also performed to detect afferent signal response during simultaneous application of two different types of sensation (pressure and vibration).

To verify that cutaneous nerves were not directly activated at high currents, trials were performed in which muscle was laid over the skin, but not mechanically coupled. Muscle stimulation was then performed, while monitoring the signal on the cutaneous nerve of the underlying skin.

Measured signals were bandpass filtered and blanked during stimulation to remove artifact from stimulation. Both raw and filtered signals were correlated during analysis to rule out false positives. Signals were normalized using peak amplitudes from each group of pooled data. Statistical analyses were performed using a student's t-test with two tails at a significance of $p<0.05$.

Mechanical Testing

In addition to reported afferent patterns from literature, to establish a baseline of the afferent response to each type of tactile sensation, afferent responses from the saphenous nerve on the contralateral limb were measured. Needle, hook, and fine wire electrodes were placed in the neuro-musculature of the contralateral limb. A mechanical arm (Aurora Scientific) was positioned to indent the medial skin on hind limb, in the area innervated by the saphenous nerve. Indentations of 0.5, 1, 2, 3, 4, and 5 mm were performed for varying durations. Vibrations of the skin was also performed at 1, 2, 4, 5, 10, 20, 30, 40, 50, 60, 70, 80, and 100 Hz using the same mechanical arm. The data from this control experiment were used to establish a baseline to which the CMI was compared.

To isolate the effect of electrical stimulation on the skin flap, mechanical actuation of the CMI and afferent recording were also performed using the same parameters described above. For this testing, the CMI was isolated and positioned on a hard surface to prevent mechanical actuation of surrounding or underlying tissues.

Sensitivity Testing

To test the effect of the CMI construction and indwelling localization on the sensitivity of the nociceptive threshold, a behavioral experiment was conducted. Firstly, CMI's were constructed in 5 rats as described above. A sham surgery was performed in 5 rats, wherein a linear incision was created on the medial aspect of the hind limb. Blunt dissection was performed to isolate and visualize the nerve. The incision was then closed using suture. All animals were allowed to recover for 14-15 days.

Calibrated forceps were utilized for assessing the mechanical nociceptive threshold (Rodent Pincher-analgesia meter, Bioseb, Pinellas Park, USA). Animals were brought to the experimental room at least 30 minutes prior to experimentation and all behavioral tests were done during the light phase. The rat was placed on the bench and loosely restrained using a towel to cover the eyes and prevent environmental stimulation. Then, the tips of the forceps were positioned over the CMI or on the corresponding skin flap in the control rats, taking care to ensure that the same tip length were applied. While access to the CMI was through the external skin, this was the closest simulation possible to apply the same mechanical pressure for control and CMI groups. Force was then manually incremented at a rate of 20 grams per second until the limb was withdrawn.

The threshold was noted and the rat was allowed to rest for approximately a minute. Measurements were repeated 5 times and the averages were compared between groups using a two-tailed heteroscedastic t-test.

Evaluation of Gross Morphology

Following all electrophysiological and biomechanical testing, the CMI was carefully dissected from surrounding scar tissues in a layer-by-layer fashion. Photographs and gross measurements were taken. Blunt scissors were used to dissect between different tissue layers under an operating microscope to determine levels of adhesion, angiogenesis, and tissue health. These observations and notes were corroborated with histological results to inform the overall tissue remodeling and structure.

Histology

Tissues from the experimental and contralateral sides were harvested and fixed in 4% formalin for 24 hours. They were then washed with PBS for 15 minutes, stored in 75% ethanol, and paraffin processed. 5 um sections were obtained every 100 um in both longitudinal and cross sectional orientations of the tissue. Tissues were stained with hematoxylin and eosin (H&E). Immunohistochemistry was performed using an s100 (ThermoFisher) primary antibody (1:100 dilution) and GFP-anti-mouse (1:200) secondary antibody to stain for cutaneous receptors. Immunofluorescence images were taken on an Evos FL Auto epifluorescence microscope (Fisher) with identical lighting conditions. Luxol fast blue staining was utilized to stain nervous tissue and dense collagen in the skin. Masson's trichrome stain was used to evaluate the fibrosis and deposition of collagen at the interface of the skin and muscle.

Alternative CMI Architectures

Alternative CMI architectures were designed to expand the modes of sensation. These geometries included 1) subcutaneous actuator (n=3), 2) sandwich actuator (n=3), and 3) conical actuator (n=3) architectures. In the subcutaneous actuator approach, the EDL was sutured to the subcutaneous layer of the skin overlaying the hind limb and actuated to induce skin strains (FIG. 16A). Following healing, only modest skin strains were observed at high muscle stimulation amplitudes (40 Hz pulses). Afferent signals were also recorded in response to the applied skin strains. However, the highly compliant nature of subcutaneous tissue and the elasticity of the skin caused a significant proportion of the muscle's actuation to be absorbed without inducing adequate skin strains. This subcutaneous actuator approach would also be inconvenient for amputations in which sockets are worn, as skin would undergo routine micromotion within the socket. In the sandwich actuator approach, the de-epithelialized skin was sandwiched between the muscle actuator and the fascia of the biceps femoris (FIG. 16B). In this configuration, contraction of the CMI muscle applies a normal force onto the skin. However, the elasticity of the fascia and small volume of the CMI muscle generated insignificant normal forces. Finally, in the conical actuator approach, muscle was conically wrapped around de-epithelialized skin such that muscle actuation caused greater radial contraction forces at the cone's vertex as compared to its base (FIG. 16C). This approach was intended to cause the skin to undergo both radial compression and axial translation in an attempt to produce both skin contact and slip. Following healing and scarring, however, the degree of slipping was significantly restricted and no detectable afferents were generated, specifically in response to axial translation. It is possible that the scale of this geometry in a rat was too small to induce movement and the lack of hair in the implanted skin minimized detection of slipping sensations.

In the future, these architectures should be investigated in a larger animal model and be expanded to include mechanisms to actuate nociceptive fibers.

Example 2. Validation of an ADI

Validation of an ADI 20 was performed in a murine model, which is shown in FIG. 3 and the results of which are shown in FIG. 4. As shown in FIG. 4, afferent signals from the skin associated with the agonist muscle were detected upon stimulation of the antagonist muscle.

While example embodiments have been particularly shown and described, it will be understood by those skilled in the art that various changes in form and details may be made therein without departing from the scope of the embodiments encompassed by the appended claims.

The teachings of all patents, published applications and references cited herein are incorporated by reference in their entirety.

What is claimed is:

1. A cutaneous mechanoneural interface, comprising:
a device in operative arrangement with a muscle actuator to stimulate contraction of a muscle of the muscle actuator, the muscle of the muscle actuator disposed mechanically in combination with a skin flap comprising at least one of a native or regenerative neurovascular structure of an amputated body segment; and
a controller in communication with the device, the controller providing a stimulation signal to the device based on a signal received from a sensor of a prosthetic device.

2. The cutaneous mechanoneural interface of claim 1, wherein the stimulation signal provides for at least one of a strain sensation, a vibratory sensation, or a sliding sensation at the skin flap by the muscle actuator.

3. The cutaneous mechanoneural interface of claim 1, wherein the stimulation signal provides for constriction or compression of the skin flap by the muscle actuator.

4. The cutaneous mechanoneural interface of claim 1, wherein the stimulation signal provides for a graded touch sensation at the skin flap by the muscle actuator.

5. The cutaneous mechanoneural interface of claim 1, wherein the muscle of the muscle actuator is disposed in a cuffed configuration about the skin flap.

6. The cutaneous mechanoneural interface of claim 1, wherein the muscle of the muscle actuator is disposed in a conical configuration about the skin flap.

7. The cutaneous mechanoneural interface of claim 1, wherein the signal received from the sensor of the prosthetic device includes at least one of pressure, shear, stress, strain, or vibration information detected at a surface of the prosthetic device.

8. The cutaneous mechanoneural interface of claim 1, wherein the device is an electrode.

9. The cutaneous mechanoneural interface of claim 1, wherein the muscle actuator is a muscle graft.

10. The cutaneous mechanoneural interface of claim 1, wherein the muscle of the muscle actuator is disposed in a circumferential configuration about the skin flap.

* * * * *